US010537702B2

(12) United States Patent
Weiss et al.

(10) Patent No.: US 10,537,702 B2
(45) Date of Patent: *Jan. 21, 2020

(54) LUCID DREAM STIMULATOR, SYSTEMS, AND RELATED METHODS

(71) Applicant: Aladdin Dreamer, Inc., Paradise Valley, AZ (US)

(72) Inventors: Craig Weiss, Paradise Valley, AZ (US); John R. Shambroom, Framingham, MA (US); Thomas Roth, Northville, MI (US); Carolyn Wong-Simpkins, Chevy Chase, MD (US)

(73) Assignee: ALADDIN DREAMER, INC., Paradise Valley, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/385,922

(22) Filed: Apr. 16, 2019

(65) Prior Publication Data
US 2019/0240444 A1   Aug. 8, 2019

Related U.S. Application Data

(63) Continuation of application No. 15/958,710, filed on Apr. 20, 2018, now Pat. No. 10,300,240, which is a
(Continued)

(51) Int. Cl.
*A61M 21/00* (2006.01)
*A61N 1/04* (2006.01)
(Continued)

(52) U.S. Cl.
CPC ............ *A61M 21/00* (2013.01); *A61M 21/02* (2013.01); *A61N 1/0456* (2013.01);
(Continued)

(58) Field of Classification Search
CPC ............................. A61M 21/00; A61M 21/02
(Continued)

(56) References Cited

U.S. PATENT DOCUMENTS 3,762,396 A   10/1973   Ballentine et al.
5,123,899 A    6/1992   Gall
(Continued)

OTHER PUBLICATIONS

International Search Report and Written Opinion for International Application No. PCT/US2016/030766, dated Jul. 11, 2016 (14 pages).
(Continued)

*Primary Examiner* — John P Lacyk
(74) *Attorney, Agent, or Firm* — Bookoff McAndrews, PLLC

(57) ABSTRACT

A method for communicating with devices may include monitoring brain activity of a subject via an EEG monitoring system coupled to the subject. The method also may include detecting a predefined state of brain activity of the subject. Further, based on the detecting the predefined state, the method may include wirelessly transmitting instructions from the EEG monitoring system to the at least one household device to adjust a setting of the at least one household device.

17 Claims, 10 Drawing Sheets

Related U.S. Application Data continuation-in-part of application No. 15/638,869, filed on Jul. 14, 2017, now Pat. No. 9,974,924, which is a continuation-in-part of application No. 15/137,136, filed on Apr. 25, 2016, now Pat. No. 9,737,683.

(60) Provisional application No. 62/158,521, filed on May 7, 2015, provisional application No. 62/531,871, filed on Jul. 12, 2017, provisional application No. 62/528,058, filed on Jul. 1, 2017, provisional application No. 62/525,287, filed on Jun. 27, 2017, provisional application No. 62/521,518, filed on Jun. 18, 2017, provisional application No. 62/521,515, filed on Jun. 18, 2017, provisional application No. 62/521,512, filed on Jun. 18, 2017.

(51) Int. Cl.
*A61N 1/36* (2006.01)
*A61M 21/02* (2006.01)

(52) U.S. Cl.
CPC ......... *A61N 1/0476* (2013.01); *A61N 1/0484* (2013.01); *A61N 1/36025* (2013.01); *A61M 2021/005* (2013.01); *A61M 2021/0016* (2013.01); *A61M 2021/0027* (2013.01); *A61M 2021/0066* (2013.01); *A61M 2021/0072* (2013.01); *A61M 2205/3553* (2013.01); *A61M 2205/3569* (2013.01); *A61M 2205/3584* (2013.01); *A61M 2205/3592* (2013.01); *A61M 2205/505* (2013.01); *A61M 2209/06* (2013.01); *A61M 2209/088* (2013.01); *A61M 2210/06* (2013.01); *A61M 2230/005* (2013.01); *A61M 2230/10* (2013.01); *A61M 2230/18* (2013.01); *A61M 2230/63* (2013.01)

(58) Field of Classification Search
USPC .................................................. 600/26–28
See application file for complete search history.

(56) References Cited

U.S. PATENT DOCUMENTS

| | | | |
|---|---|---|---|
| 8,029,431 | B2 | 10/2011 | Tononi |
| 8,239,030 | B1 | 8/2012 | Hagedorn et al. |
| 8,268,851 | B2 | 9/2012 | Kroll |
| 9,737,683 | B2 | 8/2017 | Shambroom |
| 10,300,240 | B2* | 5/2019 | Weiss .................... A61M 21/02 |
| 2004/0030258 | A1 | 2/2004 | Williams |
| 2010/0041962 | A1 | 2/2010 | Causevic et al. |
| 2011/0295083 | A1 | 12/2011 | Doelling et al. |
| 2014/0221779 | A1 | 8/2014 | Schoonover et al. |
| 2014/0343354 | A1 | 11/2014 | Larson |
| 2015/0320588 | A1 | 11/2015 | Connor |
| 2015/0343196 | A1 | 12/2015 | Vasapollo |

OTHER PUBLICATIONS

Voss et al., "Induction of self awareness in dreams through frontal low current stimulation of gamma activity," Nature Neuroscience, vol. 17, No. 6, Jun. 2014 (5 pages).

"Dream Fitness: How to Use Lucid Dreams for Weight Loss," (http://brainwavepowermusic.com/blog/blog/dream-fitness-how-to-use-lucid-dreams-for-weight-loss) last accessed May 4, 2016 (5 pages).

Adee, Sally, "Zap your brain into the zone: Fast track to pure focus," New Scientist, Feb. 2012 (6 pages).

"Lucid Dreaming FAQ," Lucidity Institute, accessed from Lucidity.com, (last modified Feb. 16, 2015) (20 pages).

Marcus, A. D., "The Weird World of Brain Hacking," WSJ Online, (Nov. 9, 2015) (4 pages).

RunPhones, "Running Headband Headphones." RunPhones.com (last accessed Jan. 16, 2017) (4 pages).

\* cited by examiner

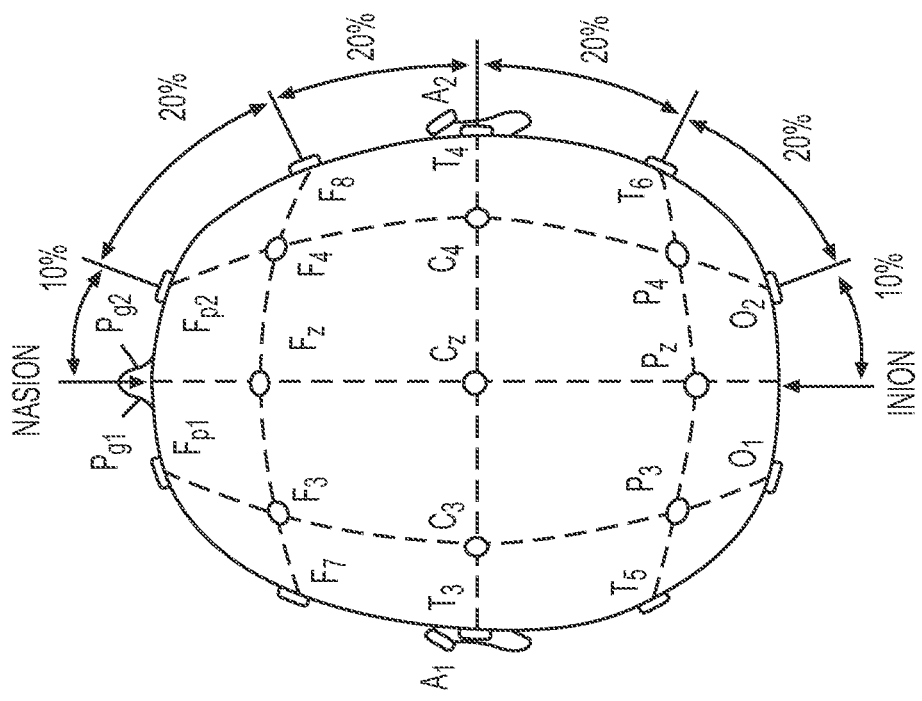
FIG. 7B *(PRIOR ART)*
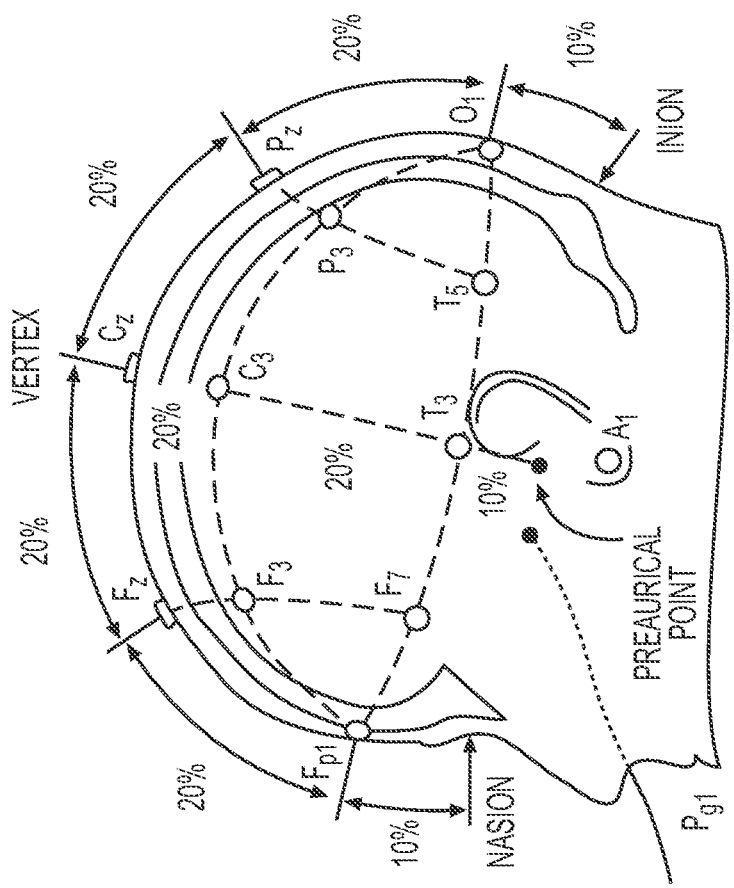
FIG. 7A *(PRIOR ART)*

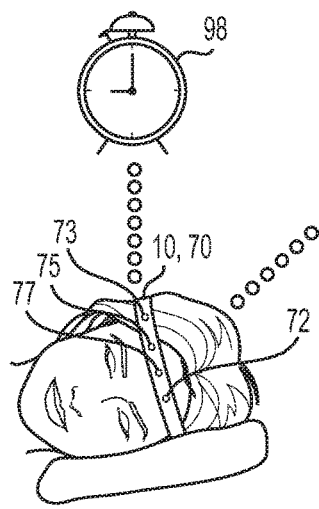
FIG. 14A
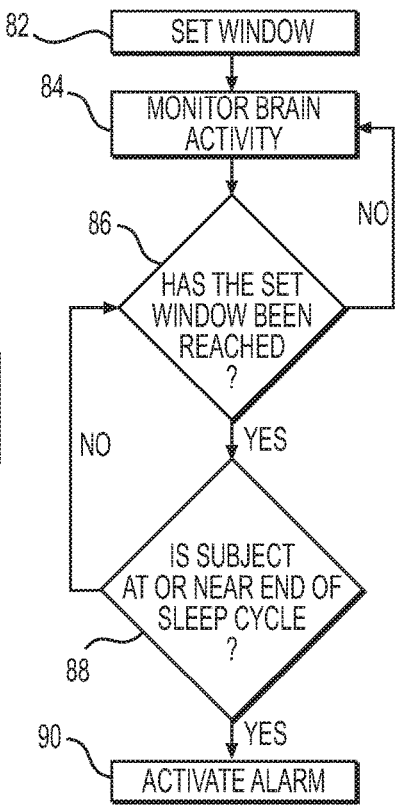
FIG. 14B
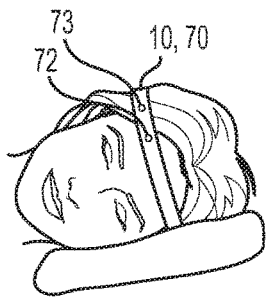
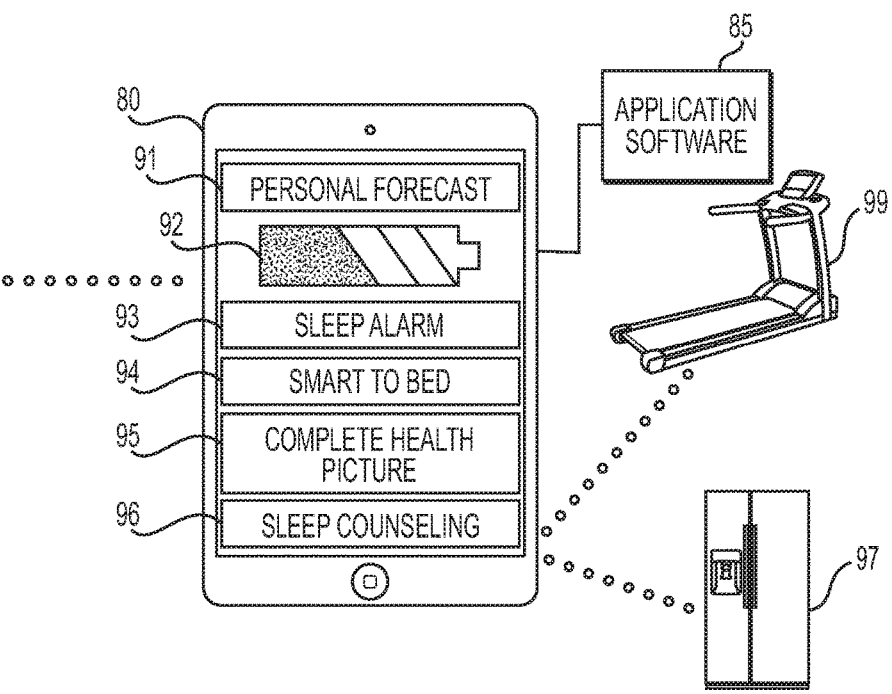
FIG. 15

LUCID DREAM STIMULATOR, SYSTEMS, AND RELATED METHODS

CROSS-REFERENCE TO RELATED APPLICATIONS

This application is a Continuation of U.S. patent application Ser. No. 15/958,710, filed on Apr. 20, 2018, which is a Continuation-In-Part of U.S. patent application Ser. No. 15/638,869, filed on Jul. 14, 2017, which is a Continuation of U.S. patent application Ser. No. 15/137,136, filed on Apr. 25, 2016, which claims the benefits of priority from U.S. Provisional Application No. 62/158,521, filed on May 7, 2015. Additionally, U.S. patent application Ser. No. 15/958,710, to which this application claims priority, also claims the benefits of priority from U.S. Provisional Application No. 62/521,512, filed Jun. 18, 2017, U.S. Provisional Application No. 62/521,515, filed Jun. 18, 2017, U.S. Provisional Application No. 62/521,518, filed Jun. 18, 2017, U.S. Provisional Application No. 62/525,287, filed Jun. 27, 2017, U.S. Provisional Application No. 62/528,058, filed Jul. 1, 2017, and U.S. Provisional Application No. 62/531,871, filed Jul. 12, 2017. The entireties of each of the above-listed applications are incorporated herein by reference.

TECHNICAL FIELD

Various aspects of the present disclosure relate generally to systems, devices, and related methods for inducing lucid dreams. More specifically, the present disclosure relates to devices, systems, and methods for stimulating portions of a subject to induce a lucid dream state in the subject, detecting stages of a subject's sleep, providing personal sleep tracking for a subject, improving a waking state and/or dream recall of a subject, detecting sleep disorders, and/or coordinating a subject's sleep state with one or more devices or systems.

BACKGROUND

Sleep is a biological necessity. Humans must sleep to maintain their health. The American Academy of Sleep Medicine ("AASM") recommends that adult humans receive seven or more hours of sleep per night. However, for some individuals, particularly those who suffer from or who may be suffering from various sleep disorders, such as sleep apnea or other sleep-related breathing disorders, insomnia, parasomnias, circadian rhythm sleep-wake disorders, and sleep-related movement disorders, this can prove difficult.

Through the use of electroencephalogram ("EEG") technology, scientists have been able to measure stages of sleep. In particular, EEG technology enables a determination to be made as to which particular stage of sleep a person may be undergoing at any given time, such as rapid eye movement ("REM") sleep or non-REM ("NREM") sleep.

Over an average life-expectancy, one could expect to sleep for approximately 20 years and dream for approximately 5 years. While the vast majority of people experience dreams passively as a quasi-random set of experiences that happen to them and over which they have very little, if any, control, some people experience lucidity during their dream state. A lucid dream is a state in which one becomes aware that one is dreaming, and in many cases, they can control the dream experience. The ability to regularly have lucid dreams is quite rare. Some people, through the use of various mental exercises, are capable of inducing a lucid dreaming experience, though this often requires extensive practice and concentration, and even still only results in occasional lucid dreams.

During typical REM sleep, one experiences a primary state of consciousness that is concerned only with the immediate present. During wakefulness, human beings experience a secondary state of consciousness that introduces higher order cognitive functions such as self-reflective awareness, abstract thinking, and access to thoughts of both past and future. One way to think of lucid dreaming is as a state of sleep in which both primary and secondary states of consciousness exist simultaneously which allows the subject to become aware of the fact that he or she is dreaming during the dream. This awareness or lucidity can also provide the subject with the ability to exert control over the ongoing dream plot.

During sleep, human beings typically enter REM sleep (e.g., dream sleep) during approximately 25% of their overall sleep time. The remainder of sleep is spent in NREM sleep. NREM sleep is made up of three stages. A person experiences light sleep in the first stage, and deep sleep in the second and third stages. During deep sleep, it is difficult to awaken a person. Following deep sleep, individuals experience REM sleep.

The average human subject sleeps in 90-minute sleep cycles, typically having about five cycles throughout the night. During these cycles, one alternates between stages of NREM and REM sleep. The first REM period typically occurs approximately 70-90 minutes after one falls asleep and may last for about ten minutes. Subsequent REM periods typically occur every 90 minutes. Subjects typically experience progressively better quality REM periods as the night goes on. Such REM periods may be of a longer duration than earlier REM periods. A subject's final REM period of the night may last for up to an hour or more.

Recently, market trends have demanded wrist-worn smart devices, typically utilizing actigraphy. Actigraphy measures a subject's movement to determine whether the subject is awake or asleep. While such wrist-worn devices may be relatively accurate in detecting movement, they are limited in that, unlike EEG technology, they cannot detect particular stages of sleep that the user may be undergoing at a given time (e.g., light sleep, deep sleep, NREM sleep, REM sleep, etc.). Accordingly, such conventional devices are further limited with respect to the amount of sleep data that can be provided to subjects.

Additionally, it is known in the art that the best time for a subject to remember their dreams is within the first ninety seconds after waking up. During this time, the ability to recall dreams (e.g., dream recognition) is enhanced by keeping the subjects body in the same position that it was in when waking up. In order to preserve the memory of the dreams recalled, subjects will often keep a dream log, with entries contemporaneously recorded at the time of recollection. It is often desired to be capable of remembering dreams, some consider dreams to be valuable and insightful while others find the ability to recall dreams as amusing, exciting, and entertaining. Other times, a subject may wish to not remember a particular or persistent dream.

According to the American Sleep Apnea Association ("ASAA"), twenty-two million Americans suffer from sleep apnea, a sleep-related breathing disorder in which a subject stops breathing periodically throughout sleep, in some cases hundreds of times during a sleep session. Breathing may be paused for durations ranging from a few seconds to more than a minute. The pauses in breathing are followed by brief moments of awakening, which can disrupt sleep. Sleep apnea can occur during any state of sleep, but it is typically most harmful during REM sleep. Common signs and symptoms of sleep apnea include loud snoring and gasping or choking sounds during sleep, waking up with a dry mouth or sore throat, morning headaches, excessive sleepiness or fatigue, insomnia, attention problems, and irritability. There are three types of sleep apnea—obstructive sleep apnea ("OSA"), central sleep apnea, and complex sleep apnea—with OSA being the most common.

It is estimated that 80% of OSA cases go undiagnosed. This may be due in part to the fact that a person suffering from sleep apnea may be unaware that he or she has the condition. Such a person may need to rely on others, such as family members or friends, to monitor him or her while sleeping, to see whether the person experiences any unusual sleep activity that may be associated with sleep apnea (e.g., breathing cessation, loud snoring, and gasping or choking sounds during sleep).

Sleep apnea disturbs sleep and affects sleep quality. Those with sleep apnea may also experience other problematic conditions. In this regard, the ASAA states that untreated OSA can lead to such problems as high blood pressure, chronic heart disease, atrial fibrillation, stroke, and other cardiovascular problems. Additionally, OSA may be associated with type-2 diabetes and depression, and may increase one's risk for premature death. As noted by the ASAA, with sleep apnea leading to drowsiness, it also has been shown to be a factor in many traffic accidents as well as accidents involving heavy machinery.

Sleep apnea is commonly treated with a continuous positive airway pressure ("CPAP") machine. Other treatments include special dental devices that are worn during sleep, avoiding sleeping on one's back, weight loss, and surgery. A potential sleep apnea patient may first visit a primary care physician ("PCP") for a consultation. The PCP may then refer the patient to a pulmonologist for another consultation, who then may prescribe that the patient undergo a sleep study in which the patient spends one or more nights at a sleep center/sleep lab for the sleep study, which typically includes a polysomnogram ("PSG"). The PSG records the patient's brain activity, eye movement, heart rate, and blood pressure, as well as the amount of oxygen in the patient's blood, air movement through the patient's nose during breathing, snoring, and chest movements. This is typically accomplished through the use of multiple sensors and other equipment connected to the patient, such as electrodes, nasal tubing, elastic belts fitted around the chest and abdomen, a finger monitor, EKG monitors, and a microphone. Following the PSG, the patient may receive a diagnosis and, if diagnosed with sleep apnea, then may be prescribed a CPAP machine.

For many people, undergoing a sleep study in a sleep center/sleep lab is not ideal. Many people find it difficult to sleep in such an environment compared to sleeping at home. To avoid the need for patient to sleep at a sleep center/sleep lab for a PSG, home-based sleep tests have been used. However, such tests do not monitor brain activity, and therefore, are not complete PSG studies.

SUMMARY

Examples of the present disclosure relate to, among other things, systems, devices, and methods for inducing a lucid dream state in a subject. Each of the examples disclosed herein may include one or more of the features described in connection with any of the other disclosed examples.

In one aspect, a dream stimulator may include a substrate and a plurality of electrodes positioned along a first side of the substrate. The stimulator also may include a stimulator coupled to the substrate. At least one lead may couple the plurality of electrodes to the stimulator. Additionally, a band may be positioned along a second side of the substrate and about each of the plurality of electrodes.

Examples of the stimulator may additionally and/or alternatively include one or more of the following features. The substrate may be flexible to permit the substrate to attain a curved shape, and the substrate may include an adhesive. The plurality of electrodes may include four electrodes aligned on an axis of the substrate, and the plurality of leads may include four leads, each of the four leads corresponding to one of the four electrodes. The electrodes, the leads, or both may be printed on the substrate. The band may include a flexible fabric that covers an entirety of the substrate. The substrate may include a first coupling mechanism having a shape corresponding to a shape of a first coupling feature of the stimulator, and the band may include a second coupling mechanism having a shape corresponding to a shape of a second coupling feature of the stimulator. The first coupling mechanism may include a plurality of posts and the first coupling feature may include channels. The stimulator also may include a sensor for measuring a physiological parameter of a subject.

In another example, a method for optimizing dream stimulation may include positioning a plurality of electrodes on a forehead of a subject. The method also may include delivering transcranial stimulation to the subject via the plurality of electrodes at a first frequency. Additionally, the method may include ceasing delivery of transcranial stimulation at the first frequency, monitoring brain activity of the subject, and delivering transcranial stimulation to the subject via the plurality of electrodes at a second frequency, different than the first frequency.

Examples of the method may additionally and/or alternatively include one or more of the following features. Monitoring brain activity may include sensing a frequency of electrical activity of the subject's brain via a sensor and the second frequency may correspond to a frequency of electrical activity sensed via the sensor. Monitoring brain activity may include determining whether a portion of the brain associated with dreaming has been stimulated to a predetermined level. The method also may include receiving feedback from the subject as to whether or not the subject had a lucid dream, and the second frequency may be based, at least in part, on the feedback. Delivering transcranial stimulation to the subject via the plurality of electrodes at least one of the first frequency or the second frequency may include delivering a stimulation waveform including two or more frequencies. Additionally, the method may include delivering transcranial stimulation via the plurality of electrodes at the first frequency at pre-programmed intervals and wherein the first frequency is between 25 Hz and 40 Hz. The method also may include determining whether the subject has entered a Rapid Eye Movement (REM) sleep period, prior to delivering transcranial stimulation at the first frequency.

In another example, a method for optimizing dream stimulation may include positioning a plurality of electrodes on a head of a subject and delivering transcranial stimulation to the subject via the plurality of electrodes at a first frequency. The method also may include ceasing delivery of transcranial stimulation at the first frequency and determining a change of frequency of brain activity of the subject from the first frequency towards a natural frequency. Further, the method may include delivering transcranial stimulation to the subject via the plurality of electrodes at the natural frequency.

Examples of the method may additionally and/or alternatively include one or more of the following features. The method may further include delivering visual or audio content relating to a topic prior to delivering transcranial stimulation at the first frequency or the natural frequency. Also, the method may include delivering transcranial stimulation via the plurality of electrodes at the first frequency at pre-programmed intervals, and wherein the first frequency is between 20 Hz and 60 Hz. The method also may include determining whether the subject has entered a Rapid Eye Movement (REM) sleep period, prior to delivering transcranial stimulation at the first frequency. The method may include sensing a physiologic parameter of the subject, and ceasing delivery of transcranial stimulation at the natural frequency based on the sensed physiological parameter.

In another example, a method for optimizing dream stimulation may include positioning a plurality of electrodes on a forehead of a subject. The method also may include delivering transcranial stimulation to the subject via the plurality of electrodes at a first frequency. Further, the method may include delivering transcranial stimulation to the subject via the plurality of electrodes at a second frequency, different than the first frequency. In addition, delivering transcranial stimulation to the subject via the plurality of the electrodes at a first frequency may be performed simultaneously with delivering transcranial stimulation to the subject via the plurality of the electrodes at the second frequency.

In another example, a method may include monitoring brain activity of a subject via an EEG monitoring system coupled to the subject. The method also may include detecting a predefined state of brain activity of the subject. Further, the method may include wirelessly transmitting instructions from the EEG monitoring system to at least one household device to adjust a setting of the at least one household device, based on the detecting the predefined state.

Examples of the method may additionally and/or alternatively include one or more of the following features. The at least one household device may include one or more of a thermostat, an HVAC system, a fan, a heater, a light, a television, an audio system, a beverage maker, a door lock, a window covering, a garage door, or an alarm. The method may further include comparing a current time with a predefined window of time, after detecting the predefined state of brain activity, determining the current time is not within the predefined window of time, based on the comparing, and delaying the instructing the at least one household device to adjust the setting of the at least one household device. Also, the method may further include comparing a current time with a predefined window of time, after detecting the predefined state of brain activity, determining the current time is within the predefined window of time, based on the comparing, and delaying the instructing the at least one household device to adjust the setting of the at least one household device. Further, the predefined state of brain activity may correspond to an EEG pattern indicative of the subject falling asleep. Additionally, the predefined state of brain activity may correspond to an EEG pattern indicative of the subject waking up from sleep. The method may include applying transcranial stimulation to the subject. Also, the setting of the at least one household device may include one or more of an on/off setting or a level setting and the method may include monitoring at least one of a temperature or a perspiration level of the subject. Based on the monitoring of at least one of the temperature or perspiration, the method may further include adjusting a comfort setting of an environment of the subject, and adjusting the comfort setting of the environment may include adjusting a temperature of the environment. Further, the method may include detecting whether a light is on or off via a light sensor associated with the EEG monitoring system.

In another example, a method may include monitoring brain activity of a subject via an EEG monitoring system couple to the subject. The method may also include detecting a change in brain activity of the subject. Further, the method may include dynamically adjusting a setting of an environment of the subject based on detecting the change.

Examples of the method may additionally and/or alternatively include one or more of the following features. The setting of the environment may include a temperature of the environment. The method may further include detecting whether a visual cortex of the subject has been shut off. Also, dynamically adjusting the setting of the environment may include changing an on/off setting or a level setting of at least one household device. Further, the detecting the change in brain activity may include detecting that the subject is falling asleep. In addition, the detecting the change in brain activity may include detecting that the subject is waking up from sleep.

In another example, a method may include monitoring the brain activity of a subject via an EEG monitoring system coupled to the subject. The method may also include monitoring at least one of a temperature or a perspiration level of the subject. Further, the method may include detecting a predefined state of brain activity of the subject. Additionally, the method may include instructing at least one household device to adjust a setting of the at least one household device based on the detecting the predefined state and/or the monitoring of the at least one of the temperature or the perspiration level of the subject.

Examples of the method may additionally and/or alternatively include one or more of the following features. The at least one household device includes one or more of a thermostat, an HVAC system, a fan, a heater, a light, a television, an audio system, a beverage maker, a door lock, a window covering, a garage door, or an alarm. In addition, the at least one household device may include a television. The method may further include pausing and/or rewinding a program displayed via the television. Also, the detecting the predefined state of brain activity may include detecting that the subject is falling asleep. Further, after detecting the predefined state of brain activity, the method may further include comparing a current time with a predefined window of time and based on that comparing, determining the current time is not within the predefined window of time and delaying the instructing the at least one household device to adjust the setting of the at least one household device. After detecting the predefined state of brain activity, the method may further include comparing a current time with a predefined window of time and based on that comparing, determining the current time is within the predefined window of time and delaying the instructing the at least one household device to adjust the setting of the at least one household device.

In another example, a method may include monitoring brain activity of a subject via an EEG monitoring system coupled to the subject. Additionally, the method may include monitoring at least one of a temperature or a perspiration level of the subject. Also, the method may include detecting a predefined state of brain activity of the subject. Based on detecting the predefined state and/or the monitoring of the at least one of the temperature or the perspiration level of the subject, the method may further include instructing at least one household device to adjust a setting of the at least one household device. Further, the method may include storing the monitored brain activity of the subject and the at least one of the temperature or perspiration level of the subject via a system synced with the EEG monitoring system.

Examples of the method may additionally and/or alternatively include one or more of the following features. The method may further include correlating EEG data received from the EEG monitoring system and the at least one of the temperature or perspiration level of the subject and based on the correlating, determining one or more patterns in the EEG data. Also, the detecting the predefined state of brain activity may include detecting that the subject is falling asleep. In addition, the detecting the predefined state of brain activity may include detecting that the subject is waking up form sleep. Further, after the detecting the predefined state of brain activity, the method may include comparing a current time with a predefined window of time. The based on the comparing, the method may include determining the current time is not within the predefined window of time and delaying the instructing that at least one household device to adjust the setting of the at least one household device. The method may also include, based on the comparing, determining the current time is within the predefined window of time and delaying the instructing that at least one household device to adjust the setting of the at least one household device. In addition, the at least one household device may include one or more of a thermostat, an HVAC system, a fan, a heater, a light, a television, an audio system, a beverage maker, a door lock, a window covering, a garage door, or an alarm.

Further, it may be understood that both the foregoing general description and the following detailed description are exemplary and explanatory only and are not restrictive of the features described herein. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" as used herein is used in the sense of "example," rather than "ideal."

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 7A and 7B illustrate the international 10-20 system for electrode placement on the scalp;

FIG. 14A illustrates an exemplary device in communication with a synced system, according to aspects of the present disclosure;

FIG. 14B illustrates an exemplary method of waking a subject, according to aspects of the present disclosure;

FIG. 15 illustrates various views of devices and systems for EEG monitoring according to one or more embodiments of the present disclosure;

DETAILED DESCRIPTION

A lucid dream stimulator device 10 (or a plurality of devices 10 in combination as described below) and method capable of stimulating the lucid dreaming state is provided. Significant utility is achieved by portable lucid dream stimulator device 10, which may be comfortably worn by a subject while sleeping. For example, device 10 may be worn and used by the subject himself or herself, at home, without medical professional supervision. That is, the device 10 may be easily and conveniently worn by the subject in the subject's preferred environment (e.g., home, hotel, family or friend's home, etc.) and at a convenient time for the subject.

Figure 1:
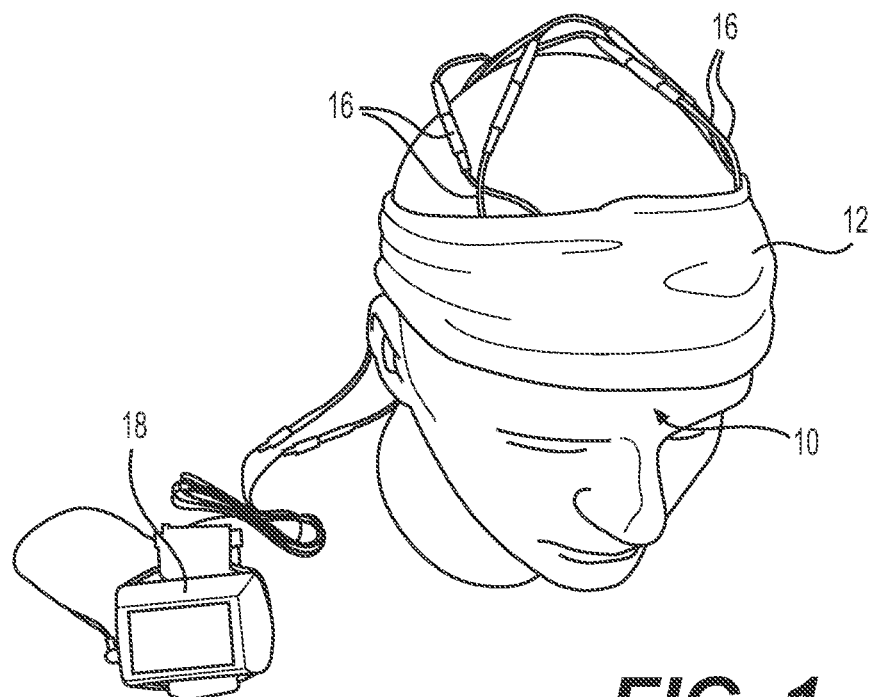
FIG. 1 illustrates an exemplary lucid dream stimulator device positioned on a model of a head.

Device 10 may include a head-worn portion as shown in FIG. 1. Device 10 may include a band 12 and a plurality of electrodes 14 (FIG. 2) coupled via electrical leads 16 to a source of stimulation 18. Band 12 may include an elastic, stretchable, or otherwise conformable strip of material (e.g., fabric). In some arrangements, band 12 may be comprised of a "breathable," light-weight, and/or loose-knit fabric so as to avoid excessive perspiration by the subject. Band 12 may be arranged so as to cover, surround, or otherwise maintain electrodes 14 in contact with the subject during use. For example, band 12 may prevent electrodes 14 from being dislodged from desired positions on the subject during use (e.g., during adjustment, shifting, turning, etc.). In additional arrangements, band 12 may be omitted.

Electrodes 14 may include an adhesive on one or more portions or sides of electrodes 14. Accordingly, electrodes 14 may be supplied with a removable liner thereon to prevent inadvertent adhesion to one or more portions of the subject or device 10. In some embodiments, electrodes 14 may be "dry" electrodes. The "dry" electrodes 14 may comprise silver nanowire or other material with sufficiently low skin impedance. One or more of the electrodes 14 may be a "wet" electrode that includes an adhesive or a gel that conditions the skin and helps lower the impedance between the electrode and the skin. In some embodiments one or more of the electrodes 14 may be "wet" electrodes and one or more electrodes 14 may be "dry" electrodes. In such embodiments, the "wet" electrodes 14 and "dry" electrodes 14 might perform different functions. For example, the "wet" electrodes 14 may provide electrical stimulation to one or more areas of the brain and the "dry" electrodes 14 may monitor the activity of one or more areas of the brain, as described in greater detail below.

Figure 2:
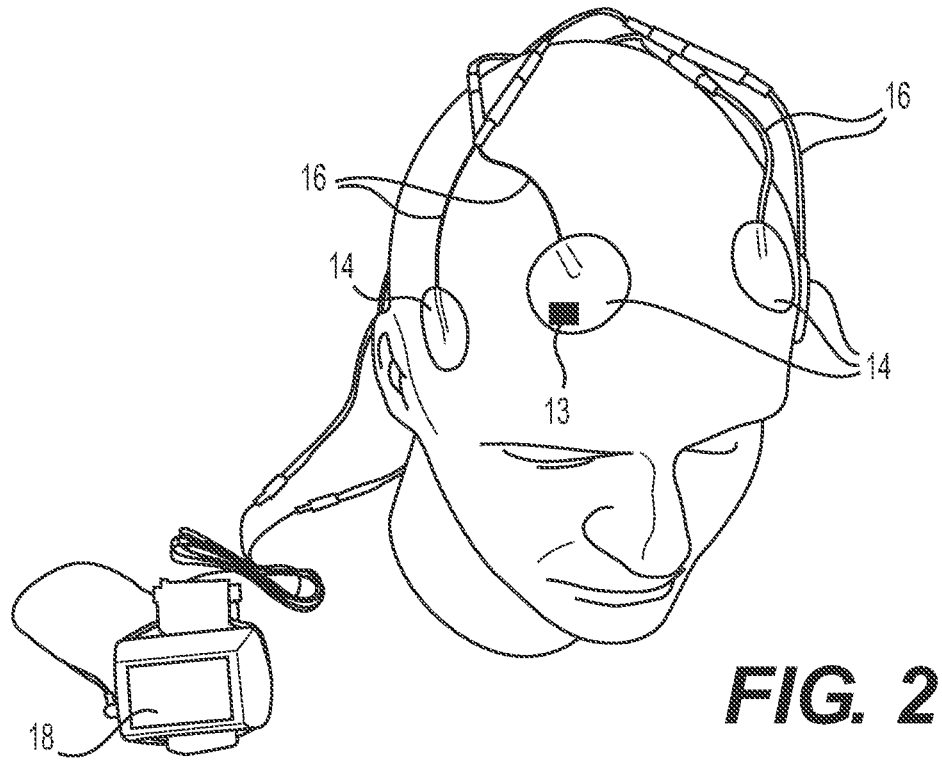
FIG. 2 illustrates a view of the exemplary lucid dream stimulator device of FIG. 1, in which a headband of the stimulator device has been removed.

Electrodes 14 may be arranged, as shown in FIG. 2, to provide electrical stimulation to at least one of the temporal and frontal areas of the brain of the subject. A standardized international 10-20 system for defining electrode 14 locations on the scalp is shown in FIGS. 7A and 7B. The system defines the locations based on the percentage of distance between certain fiducial points, including the nasion, the inion, and the overall circumference of the head. Positions are labeled F for frontal, C for central, P for parietal, O for occipital, and T for temporal, and are numbered front to back with odd numbers on the left and even numbers on the right. In instances in which intermediate positions are utilized, such positions are prefaced with the letter A. In the 10-20 system, electrode locations are defined as a percentage (either 10% or 20% depending on the location) of the circumference around the head, or the distance between certain anatomical features, namely the nasion and the inion. As such, electrode 14 spacing varies depending on the anatomy of a particular subject.

Figure 13:
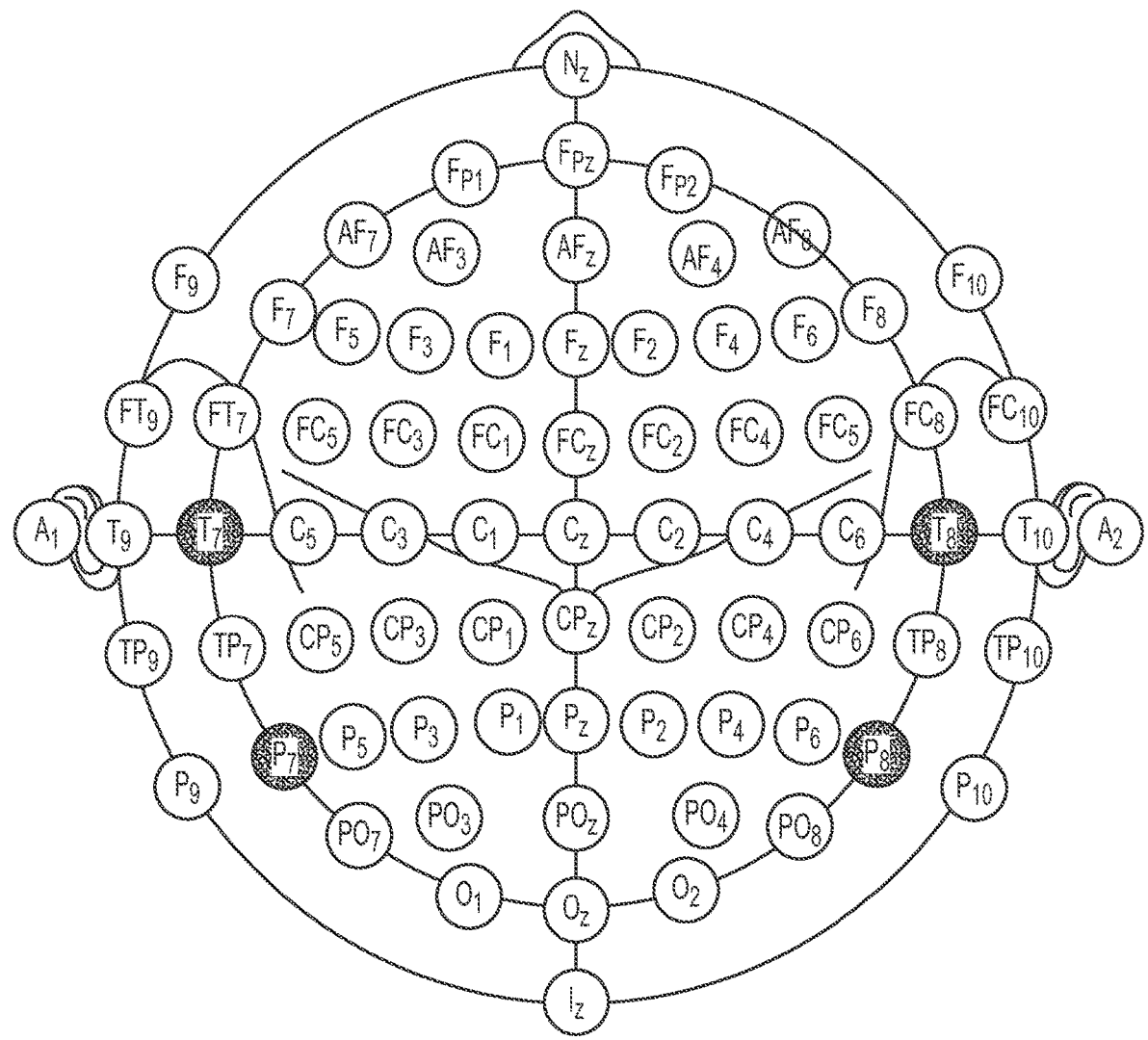
FIG. 13 illustrates the international 10-10 system for electrode placement on the scalp.

Returning to FIG. 2, four electrodes 14 are positioned along the forehead and temples of the subject for delivery of trans-cranial stimulation localized to the frontal cortex. It is understood that while four electrodes 14 are illustrated, fewer or more electrodes 14 may be positioned for delivery of trans-cranial electrical stimulation of the subject's brain. In some arrangements, for example, between two and about ten electrodes 14 may be positioned on the subject without departing from the scope of this disclosure. As used herein, the terms "about," "substantially," and "approximately," may indicate a range of values within +/−20% of a stated value. In some arrangements, all electrodes 14 may be positioned on the forehead or temples of a subject. In the example shown in FIG. 2, two forehead electrodes 14 may be positioned proximate to a subject's hairline, with each electrode 14 being approximately above one of the subject's eyes, and within a distance of approximately 8 centimeters above the center of the eyes. In addition, two temple electrodes 14 may be positioned approximately along a center-line of the forehead, just inside the hairline, preferably not more than 18 centimeters apart. That is, electrodes 14 may be located at the F7, F3, F4, and F8 (left to right) locations according to the standardized 10-20 system depicted in FIGS. 7A and 7B. Alternatively, electrodes 14 may be located at intermediate locations identified in a higher special resolution 10-10 system (FIG. 13), including the F7, AF3, AF4, and F8 locations. As shown in FIG. 13, the AF3 position may be located midway between the Fp1 and the F3 locations, while the AF4 position may be located midway between the Fp2 and F4 locations. Electrodes may be located as close to these positions as possible while avoiding the hairy areas of the scalp. That is, in some arrangements, none of electrodes 14 are positioned behind the ears, for example, of the subject. In other arrangements, electrodes 14 may additionally or alternately be positioned in the mastoid and/or precuneus regions. Further, in some further aspects of this disclosure, electrodes 14 may be arranged for delivery of transcranial stimulation in the prefrontal cortex, including the dorsolateral prefrontal cortex. Additionally or alternatively, electrodes 14 may be arranged so as to induce electrical activity in the cuneus of a subject's brain. In such an arrangement, transcranial stimulation of different portions of the subject's brain may induce different effects.

The left and right hemispheres of the brain process information in different ways. The left hemisphere tends to be analytical, while the right hemisphere tends to be more creative. As such, stimulating each of the left and right hemispheres may have different effects. For example, stimulating just the left hemisphere may prompt the subject to analyze the content of a dream, and come to the conclusion that he or she is dreaming, one of the hallmarks of lucidity. Also, the hemispheres may be differently stimulated to induce different aspects in the dream, for example the optimization of right sided stimulation to enhance dream content may be different than optimization of the left side to promote awareness of dreaming. Optimization parameters may include, but are not limited to, timing, frequency, intensity. Since stimulation may differ between the left and right hemispheres, electrode 14 placement may not be symmetric about a centerline that divides the subject's head into hemispheres. Additionally, the number of electrodes 14 on each hemisphere may differ. For example, three electrodes 14 may be positioned on the left hemisphere while one electrode 14 may be positioned on the right hemisphere, or vice versa.

Figure 4:
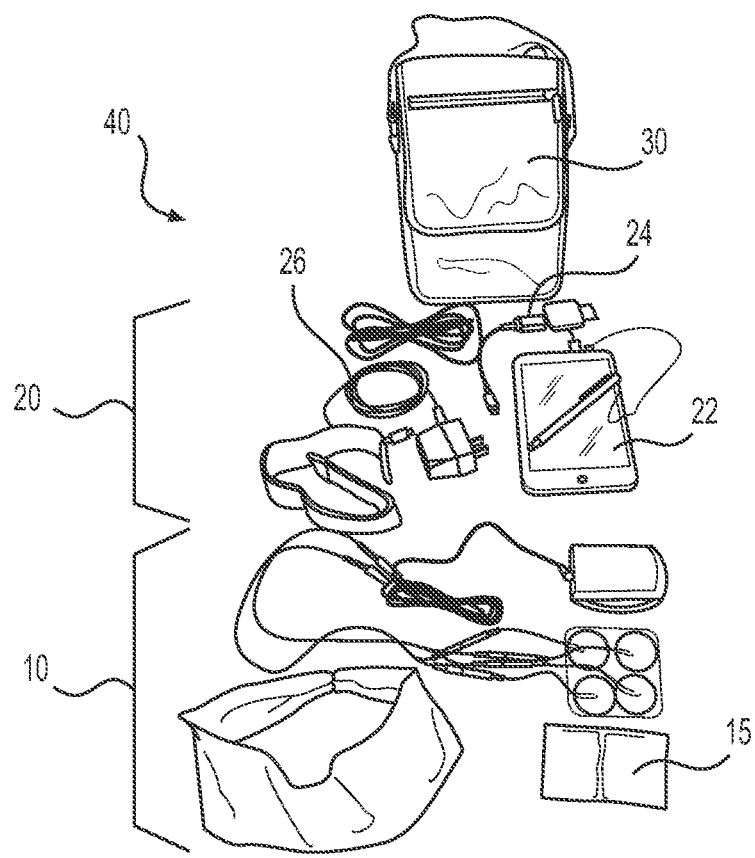
FIG. 4 illustrates an exemplary kit including the lucid dream stimulator device of FIG. 1.

Each electrode 14 may be disc-shaped as shown in FIG. 2. However, electrodes 14 may have any shape suitable for delivery of stimulation energy to (or monitoring of brain activity of) the subject, such as, for example, rectangular, ovular, square, triangular, polygonal, or irregular shapes. In addition, electrodes 14 may have a size (e.g., area) of about 1.0 inches-square (6.5 cm$^2$) to about 4.0 inches-square (25.8 cm$^2$). In one exemplary arrangement, electrodes 14 may be circular and have a diameter of about 1.25 inches (31.75 mm). While each electrode 14 as shown in FIG. 4 is depicted as having a common shape and size, it is understood that at least one or more of electrodes 14 may have varied shapes and/or sizes without departing from the scope of this disclosure.

As noted above, electrodes 14 may be arranged for trans-cranial electrical stimulation to the frontal lobes of the brain. However, it should be clearly understood that substantial benefit could be derived from an alternative arrangement of the present disclosure in which electrical stimulation is provided by means other than through electrodes 14, such as through a conductive band or some other means. Further, in some arrangements, one or more of electrodes 14 may include a sensor 13 (schematically illustrated in FIGS. 2 and 3). Sensor 13 may measure one or more behavioral or physiological activities of the subject, such as what sleep stage the subject is in, or whether the subject is in REM sleep in particular. In other arrangements, however, such sensors 13 may be separate and discrete from electrodes 14. Sensor 13 may also measure or detect movement of the subject, and electrodes 14 may provide stimulation during only periods in which sensor 13 detects a lack of movement. Also, sensor 13 may measure or detect undesirable changes in physiological parameters (e.g., a large, predetermined increase in heart rate), and device 10 can be configured to cease stimulation upon that detection.

Figure 3:
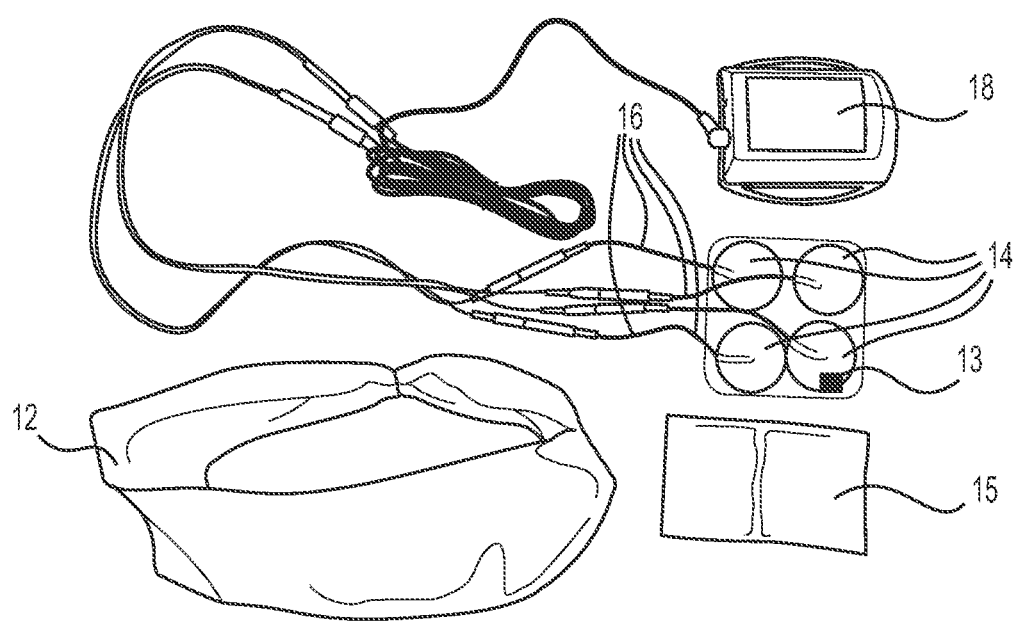
FIG. 3 illustrates components of the exemplary lucid dream stimulator device of FIG. 1 uncoupled from the model of a head.

As shown in FIGS. 1-3, electrodes 14 are coupled to a stimulator 18 via one or more electrical leads 16. Electrodes 14 may be constructed from a conductive material such as stainless steel, copper, and/or tin, and may be plated with nickel or other materials. Electrodes 14 may be a laminate including a cloth backing, a conductive carbon layer, and a suitable conductive gel (e.g., hydro-gel). Electrodes 14 may include a sponge that when wetted with a salinated solution becomes conductive. Alternatively, electrodes 14 may be incorporated onto a common substrate (e.g., substrate 60 shown in FIGS. 9-12B). The substrate 60 may be made of mylar, polyester, or other suitable material. Optionally, electrodes 14 may be printed on the substrate 60. Printing materials may include silver ink, silver/silver-chloride, copper, conductive carbon, or other such conductive materials. Additionally, a suitable conductive liquid or gel can be incorporated. Leads 16 may be printed on the substrate as well using any suitable conductive material (FIG. 11), as will be described in further detail below.

Stimulator 18 may be any appropriate stimulation source for delivery of electrical energy to electrodes 14. For example, stimulator 18 may include a Transcutaneous Electrical Nerve Stimulation (TENS) device. Stimulator 18 may be battery-operated or may draw energy through a household electrical outlet. Stimulator 18 may include an electronics module (not shown) and may generate and deliver current through leads 16 to electrodes 14 for delivery to the subject. Stimulator 18 may be configured to modulate pulse width, frequency, and intensity to suit a particular application or subject's preferences. The electronics module of stimulator 18 may include a wireless chip or other such device for wirelessly communicating with a tablet 22, as described in further detail below. Stimulator 18 may be configured for Transcranial Direct Current Stimulation (tDCS). In some arrangements, however, stimulator 18 may be configured for Transcranial Alternating Current Stimulation (tACS). It has been observed that tACS may enable improved effectiveness and specificity of stimulation via electrodes 14.

In arrangements in which stimulator 18 is configured for delivery of tACS, the electrical current delivered from stimulator 18 may flow into the body of the subject through one or more electrodes 14, and out of the body of the subject through one or more different electrodes 14. Unlike Transcranial Direct Current Stimulation (tDCS), which has a defined polarity, and therefore, both a cathode and anode electrode, tACS has alternating polarity. Therefore, the electric field and consequent effect on the brain region under each electrode 14 is more or less equivalent.

Figure 5:
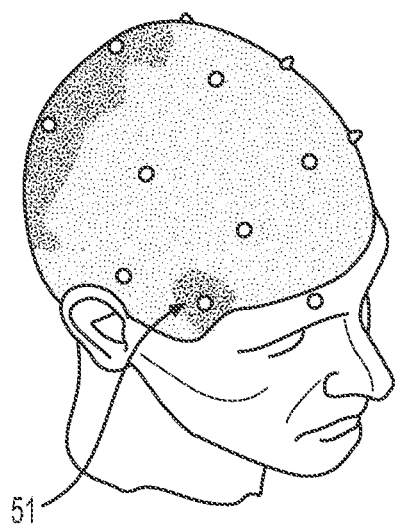
FIG. 5 is a visual representation of the brain activity observed during spontaneous lucid dreaming.

Arrangements of the present disclosure may improve, or adjust locations of, brain activity during lucid dreaming. For example, FIG. 5 illustrates brain activity zone 51 (e.g., relative electrical activity) observed during spontaneous lucid dreaming, e.g., lucid dreaming without electrical stimulation. As shown, brain activity zone 51, having a relatively higher localized electric activity, is lateral to the temples of the subject. The occipital area of the head, in particular the cuneus, is also displaying higher localized activity, which may be due to an increase in activity of the visual cortex.

Figure 6A:
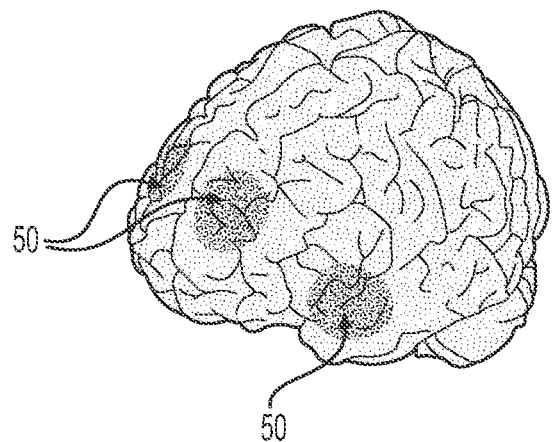
FIGS. 6A and 6B illustrate visual representations of the concentration of stimulation produced in a subject via the lucid dream stimulator of FIG. 1, when the stimulation is delivered to the subject in a variety of locations.
Figure 6B:
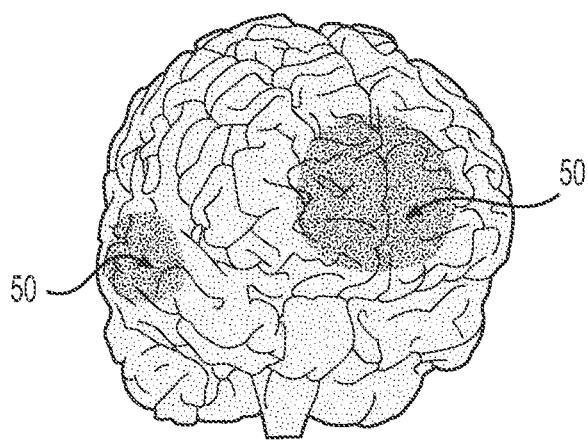

FIGS. 6A and 6B illustrate the brain stimulation zone 50 produced in a subject via the device 10 of FIG. 1, when stimulation is delivered to the subject in a variety of locations. For example, in the arrangement of FIG. 6A, four electrodes 14, including a pair of interconnected electrodes 14 may be located at the AF3 and AF4 locations, with interconnected return electrodes 14 located at the F7 and F8 locations. In such an arrangement, the stimulated potentials are relatively higher at the two frontal locations just lateral to the midline under positions AF3 and AF4, as shown in FIG. 6A. Likewise the left and right (not shown) fronto-temporal regions exhibit relatively higher potential under electrodes 14 at positions F7 and F8, as shown in FIG. 6A. In an additional arrangement, three electrodes 14, including a single electrode 14 located at the Fpz location (e.g., midway between the Fp1 and Fp2 locations) (FIG. 13), or alternatively at the AFz location (e.g., midway between the Fpz and the Fz locations) (FIG. 13), and return electrodes 14 may be located at the F7 and F8 locations. In such an arrangement, the stimulated potentials are relatively higher at the frontal location near the midline, as shown in FIG. 6B. Likewise the right and left (not shown) fronto-temporal regions exhibit relatively higher potential under electrodes 14 located at the F7 and F8 positions, as shown in FIG. 6B. As shown, stimulation potential of stimulation zone 50 of FIG. 6B is larger or wider spread than brain activity or stimulation zone 50 of FIG. 6A. Stimulation with electrodes 14 at the locations described in connection with FIG. 6A may be preferred since such an arrangement results in stimulation of the targeted, specific, or limited areas that become active during spontaneous lucid dreaming (e.g., as shown in FIG. 5). However, stimulation with electrodes 14 at the locations described in connection with FIG. 6B may be preferred because the larger inter-electrode 14 distance may enable the stimulus current to travel deeper into the brain, eliciting a more vigorous response in some subjects. While the description above details positioning of electrodes 14 along certain points of a subject's scalp, it is to be understood that these locations may vary from person to person depending on the anatomy, size, or features of an individual subject's scalp. Accordingly, in some arrangements, electrodes 14 may not be positioned precisely on the locations identified by the 10-20 or 10-10 systems. In such arrangements, electrodes 14 may be located as closely as possible to the identified positions, while remaining out of the hairline of the subject. Further, while the above noted electrode 14 positions are described, the disclosure is not so limited. Rather, electrodes 14 may be positioned in other arrangements, such as on the mastoid of a subject. In such an arrangement, electrodes 14 may be positioned at the A1 and/or A2 locations (e.g., the earlobes), as identified in both the 10-20 and 10-10 systems. However, it is understood that in some arrangements, electrodes 14 may be positioned on the bony joint just behind the ears of a subject. Such positions may be identified as the M1 and M2 locations (not shown).

In one exemplary arrangement, device 10 may provide electrical stimulation in the gamma frequency band, between about 10 Hz and about 100 Hz, for example, between about 20 Hz and about 60 Hz, or between about 25 Hz and about 40 Hz. During a subject's dream state, this frequency range may activate, excite, or otherwise stimulate the executive ego functions (e.g., self-awareness) that are also observed during wakefulness. The optimal frequency for eliciting these effects may differ from subject to subject, e.g., it may be about 42 Hz for one subject and about 38 Hz for another subject. It is therefore advantageous for the device 10 to optimize the frequency for the individual user. This can be done by stimulating at a particular frequency and gauging the effects. The effect may be assessed by soliciting feedback from the user as to whether or not they had a lucid dream. Alternatively, a sensor may measure electrical activity of the brain before, during, or after stimulation to assess the effects. The excitation frequency may be adjusted to improve effectiveness. In addition, stimulation in the high beta band may impart a sense of control over the storyline or actions in a dream, for example at or near an excitation frequency of about 25 Hz. In a preferred arrangement, the stimulation waveform may incorporate two or more frequencies to potentiate multiple effects. It should be understood that while a stimulation frequency range between about 10 Hz and about 100 Hz, a stimulation frequency range between about 20 Hz and about 60 Hz, and/or a stimulation frequency range between about 25 Hz and about 40 Hz, may be particularly useful, substantial benefits may be derived from an alternative arrangement in which the stimulation frequency deviates, even substantially, from the above-noted frequency ranges.

In one exemplary arrangement, device 10 may alter the frequency during stimulation. For example, a certain subject's optimum stimulation frequency may be unknown. Device 10 may alter the frequency around the typical or average frequencies known to induce lucid dreaming in a sample of subjects. Device 10 may begin stimulation at 38 Hz for 5 seconds, then move to 39 Hz for 5 seconds, and so on until it finishes stimulating at 42 Hz.

In use, the subject may clean a surface area of skin prior to application of electrodes 14 on the subject. For example, in order to remove dirt, oil, and/or dead skin, which may impede delivery of energy via electrodes 14, the subject may wash, exfoliate, and/or sterilize the skin. For example, the subject may use one or more alcohol pads 15 to clean the skin. With proper cleansing, impedance to each electrode 14 may be reduced to between about 5 k$\Omega$ and about 100 k$\Omega$. In addition, to facilitate efficient delivery of energy via electrodes 14, an area of skin may be wet or otherwise lubricated with an electrically conductive material. Such materials may include saline, water, and/or hydrogel.

Device 10 may be configured to determine when the subject has entered a REM (Rapid Eye Movement) period. As such, device 10 may be configured to activate electrical stimulation via electrodes 14 only during periods (or parts of periods) of REM sleep. Determination of whether the subject is in REM sleep may be accomplished by sensor(s) 13 which may be positioned on, adjacent, or otherwise near electrodes 14. However, substantial benefit may be provided by an alternative arrangement in which either there is no REM monitoring, or in which assessing REM sleep is accomplished by some other means, such as a sleep mask capable of using IR or other sensors to detect rapid eye movement, and/or another sensor capable of detecting EEG sleep frequencies and/or muscle tone otherwise associated with REM sleep. In arrangements wherein REM monitoring is accomplished by a separate device, communication between the devices may be provided. The device also may be used without REM monitoring and instead provide the electrical stimulation at pre-programmed intervals or simply on a timer (e.g., so as to coincide with normal circadian times of REM sleep (e.g., 5-8 AM)).

The device 10 may be portable and wireless, and capable of being recharged by the subject when not in use (e.g., when the subject is not sleeping). In some arrangements, device 10 may be synced with a smartphone, tablet, smart watch, computer, or other electronic device or system 20 (FIG. 4) having an application capable of receiving and transmitting data wirelessly to device 10. In some arrangements, however, delivery and transmission of data may be done via a wired connection. By way of example only, the system 20 may include a tablet 22 (e.g., iPad™), a data transmission, downloading, or synching connection 24, and a power adaptor 26. As shown in FIG. 4, the entire system may be prepared and packaged as a kit 40 in a portable carrying case or bag 30. For example, kit 40 may include device 10, any required cleaning supplies (e.g., alcohol pads 15), and electronic system 20. The application of electronic system 20 not only would track the subject's sleep patterns, but may also instruct device 10 to vary the frequency and/or duration of the electrical stimulation to achieve a subject-specific optimal lucid dreaming experience. Such duration and frequency adjustments may be part of pre-programmed patterns established as optimal, or may be altered/adjusted by the subject based on their feedback. After awakening, the subject may provide input to device 10 either directly into a subject interface on stimulator 18 of device 10, or via tablet 22 specifying his/her sleep experience. The subject may answer questions relating to his/her dreams, length, and/or quality, and/or the subject may indicate specific technical adjustments (e.g., increase/decrease frequency/duration).

In an alternative arrangement, the device 10 may be powered by a subject's smartphone, tablet 22, or other personal computing device. In such an embodiment, electrodes 14 may be wired directly into a smartphone (e.g., via one or more of a headphone jack and power port such as USB or lighting, etc.) or device 10 may be recharged by the smartphone but still capable of wireless power when in use. In these embodiments, device 10 may comprise one or more electrodes 14 that may be placed on the subject's head and capable of being recharged (e.g., via a wall outlet, smartphone, etc.), or electrodes 14 may be wired directly to a smartphone, tablet 22, or other personal computing device that is capable of both providing power as well as enabling data communication.

Placement of the head-worn device on the subject and/or selection of a stimulation frequency level or range (as, for example, described herein) may also need to be adjusted on a subject-by-subject basis. Optimal placement may be achieved through subject customization achieved based on subject feedback, either directly into stimulator 18 of device 10 or through use of an application of electrical system 20 (e.g., via tablet 22). For example, a subject, after awakening, preferably would indicate to an application on their smartphone, tablet 22, computer, smart watch, or the like to indicate the quality of their sleeping and dreaming experience. Upon receipt of inputs, recommendations for adjustments to the number and/or placement of electrodes 14, stimulation frequency and/or amplitude, the times to initiate stimulation, and/or the duration of stimulation may be suggested automatically by the application until optimal placement and stimulation is achieved to provide maximal lucid dream induction and minimal sleep disruption.

It should also be understood that one or more portions (e.g., electrodes 14 and/or band 12) of device 10 may be disposable in nature, so that it may be used by a subject for as little as one night or perhaps between 1 week and 3 months. In this way, the subject may avoid the need to clean device 10 and instead simply dispose of it and replace it with a new device 10 if and when the contacts, electrodes 14, or some other aspect of device 10, such as band 12 or sleeping cap, became dirty. Alternatively, the areas of device 10 that make contact with the subject may be cleaned, and device 10 may be reused. This may be accomplished a number of ways, such as by having electrode 14 contacts be detachable and cleanable so that they may then be reattached following sterilization.

While device 10 may be designed for the induction of lucid dreaming, it is within the scope of this disclosure that other non-lucid-dreaming benefits may be achieved by the same device. For example, it may be possible to use device 10 and transcranial electrical stimulation to provide neurofeedback, Eye Movement Desensitization and Reprocessing (EMDR), bio-feedback, or other treatments.

A further arrangement may include the use of an application located on a smartphone, tablet 22, computer, smart watch, device 10 itself, or the like that can be used by the subject prior to use of device 10 to improve the lucid dreaming experience by allowing the subject to view various videos, images and/or text prior to initiating sleep. For example, a subject who is interested in having lucid dreams about Venice, Italy may view videos, images, text, music or other content relating to Venice prior to sleep, which in combination with device 10 may improve the lucid dreaming experience. Another example might be for a subject interested in having one more lucid dreams in which the subject can fly. In such a scenario, the subject may watch content relating to flying. If someone wishes to see or meet with someone (alive or dead) during their dream, they may view content relating to that person (e.g., Albert Einstein, President of the U.S., a deceased loved one, etc.). To that end, the subject may customize the application to load their own content (e.g., pictures of a loved one). In a preferred embodiment, the application would have a social networking component in which other subjects may post their own content for use by others. For example, a subject who just finished mountain climbing may post video of their exploits in order for another subject to have images that may be incorporated into their lucid dream. It should be understood that the application concept described herein, including the social networking aspect, may be used separate and apart from device 10 as a method for improving one's dream experience.

In addition, an application of electrical system 20 may provide content for a guided meditation, sounds that evoke specific memories or images, instruction, or other audio content that the subject may listen to immediately preceding, or during, sleep to achieve a positive and desired lucid dreaming state. Such content may also be integrated into one or more portions of device 10 itself (e.g., electrodes 14, band 12, etc.), either stored locally on the device or streamed to device 10 from another device. In this arrangement, device 10 may have speakers, headphones, ear buds or the like, or alternatively, audio equipment may be provided separately and used in conjunction with device 10.

In order to induce lucid dreaming of a subject, electrical stimulation may be provided to at least one of the frontal, temporal, mastoid, and precuneus regions (e.g., lobes) of the subject's brain during REM sleep. Providing such electrical stimulation may include positioning a device (e.g., sensor 13 or other such device) capable of detecting when a subject enters REM, using the indication that the subject has entered REM to initiate electrical stimulation via electrodes 14 for at least some period of the REM sleep period, and terminating the electrical stimulation once it is detected that the subject is no longer in REM sleep.

There are a variety of benefits associated with lucid dreaming. There are significant psychological and/or therapeutic benefits associated with consciousness in the dream state. For subjects with persistent nightmares, PTSD, schizophrenia or other emotional issues that manifest themselves in the dream state, the ability to take control over a negative dream experience and overcome nightmares can be very empowering, turning a negative emotional experience into a positive one. That is, a method may include improving "positivity" or reducing anxiety of one's dreams. As such, the method may include inducing lucidity in dreams, even if just awareness or dissociation without control, thereby enabling a subject to reduce anxiety associated with anxiety producing dreams (e.g., an overachiever dreaming of being unprepared for an examination, etc.). Awareness that the anxiety causing dream is not reality may immediately reduce anxiety.

In some exemplary arrangements, one or more portions of device 10, such as sensors 13 or electrodes 14, may enable bio-feedback of physiological responses to stimulation. For example, a method may include an initial stimulation via electrodes 14 to induce a lucid dream state in a subject at a pre-determined frequency, e.g., 25 Hz. Next, the initial stimulation may be discontinued, and brain activity may be monitored via, for example, sensors 13 and/or electrodes 14 to determine whether the subject's brain organically (e.g., naturally) migrates toward a different frequency (e.g., 24 Hz, 26 Hz, 40 Hz, etc.) other than the frequency of the initial stimulation. Then, the next stimulation by device 10 may be calibrated to be delivered at the frequency the subject's brain migrated towards. That is, device 10 may recalibrate itself to best suit each individual subject's biological preferences. Such recalibration may be effective to improve inducement of lucid dreaming in the subject. In other words, the device may "jump-start" brain activity in portions of the subject's brain (e.g., the temporal-frontal cortex), then cease stimulation and monitor brain activity in order to determine the subject's own individual optimal brain frequency, and then adjust as appropriate to stimulate at the optimal brain frequency identified. As such, device 10 may maintain lucidity as naturally as possible for an individual subject.

In another exemplary method, the subject may be prompted to or independently think of certain subject matter, such as, for example, calming memories or thoughts. The subject may then use a smartphone, tablet 22, computer, device 10 itself, or the like to view visual feedback. Such visual feedback may include, for example, dynamically moving colored lights or other such visual displays. The subject's brain wave pattern may be monitored through any appropriate means (e.g., sensors 13 or the like). If the subject's brain wave pattern strays from the preferred or optimal pattern (e.g., the calming memories or thoughts), then the subject may receive visual (e.g., bio) feedback of a different sort, for example, black and white images, less or not dynamic, smaller, etc. Such a method enables the subject to condition their brain waves to the preferred/optimal patterns. Use of bio-feedback in device 10 may be applicable for the treatment of a wide array of conditions including, for example, insomnia, depression, anxiety, etc. Such conditions may or may not be directly related to lucid dream stimulation.

Another benefit to lucid dreaming comes from the ability to practice or rehearse waking activities while in the dream state. This has been proven to improve performance of the same activity during the waking state, including recovery from injury and weight loss. Dreamers have been known to rehearse various activities, such as specific athletic activities, public speaking, playing a musical instrument, etc. Because brain activity during the dream state may be similar to brain activity during the waking state, neural pathways created during practice or activity can be established in the dream state in preparation for performance in the waking state.

Figure 8:
FIGS. 8-12B illustrate various views of an additional stimulator device, according to further aspects of the disclosure.
Figure 9:
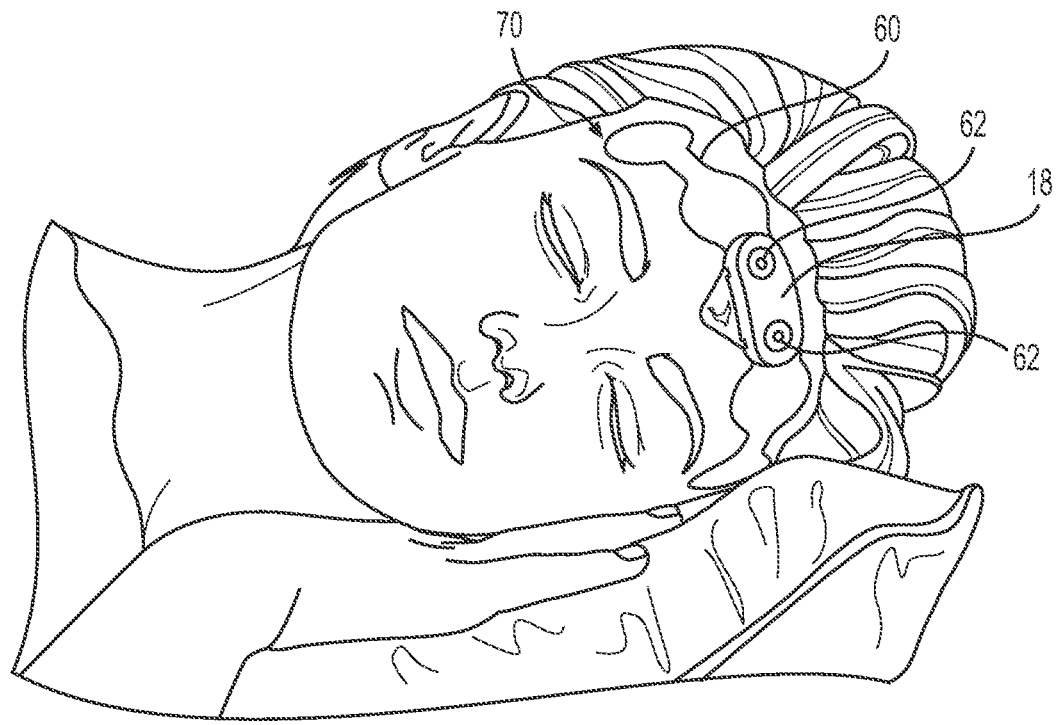
Figure 10:
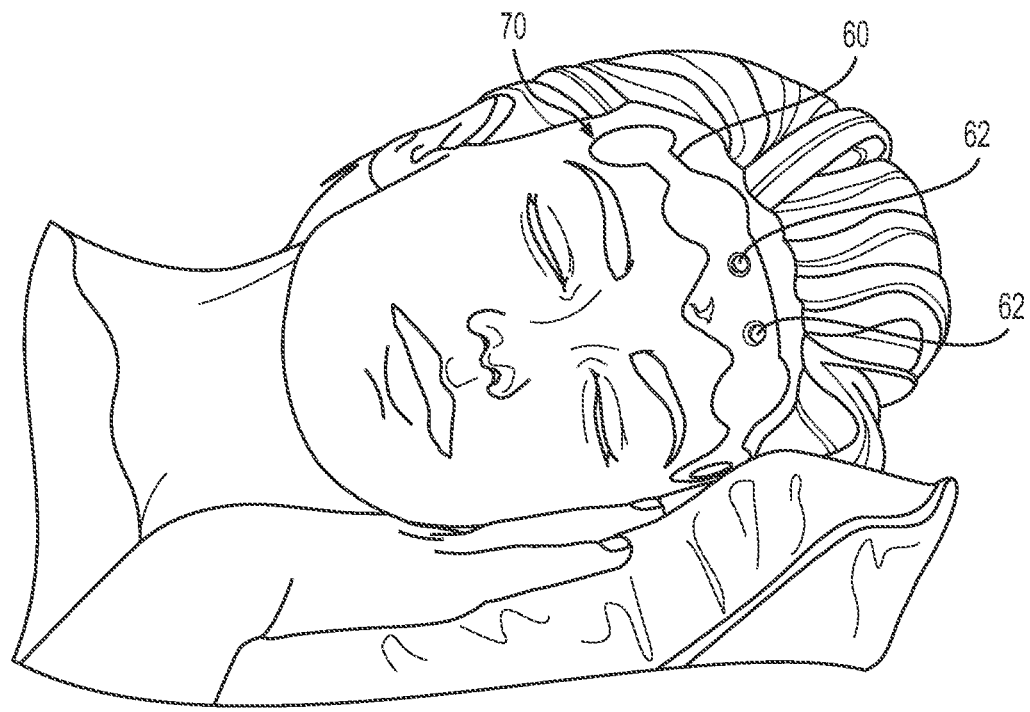
Figure 11:
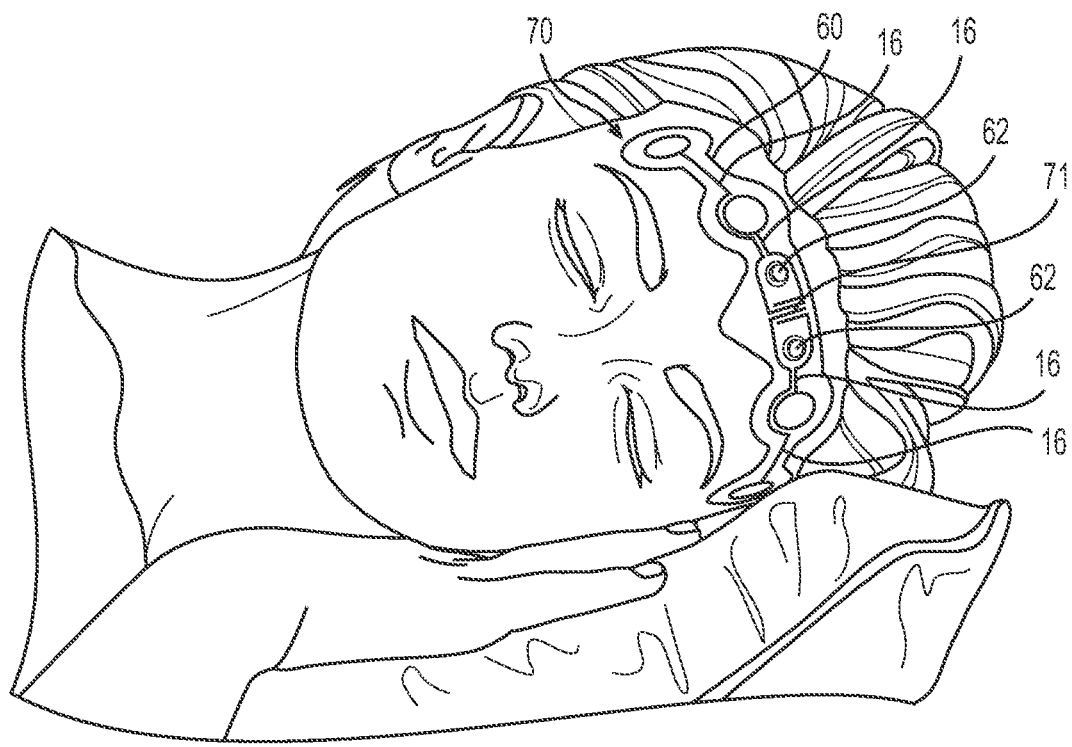
Figure 12A:
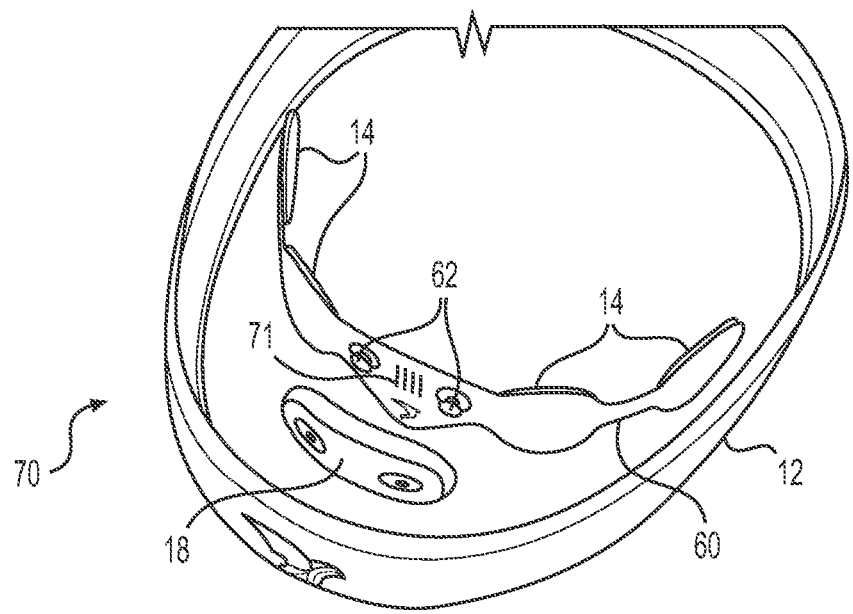
Figure 12B:
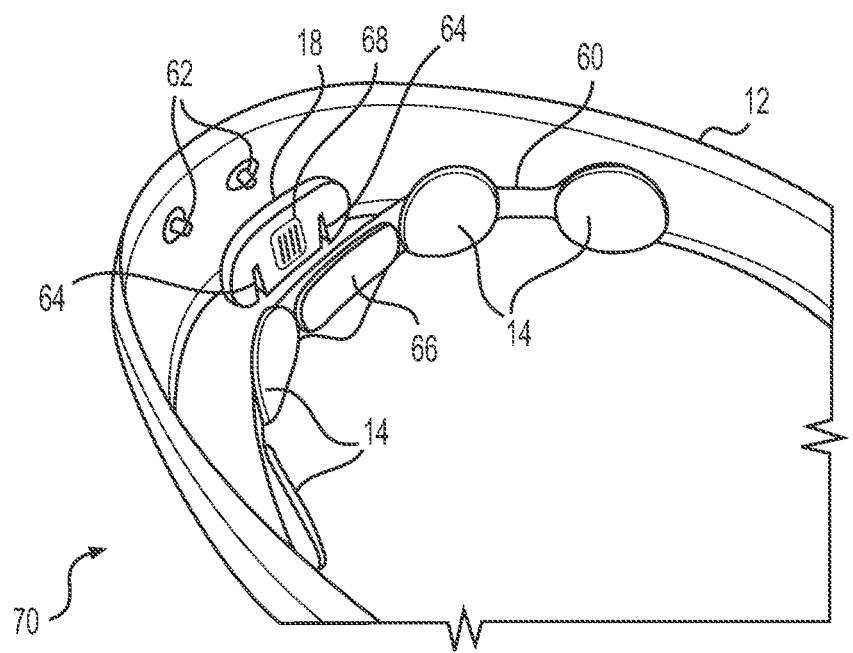

FIGS. 8-12B illustrate various views of an additional stimulator device, according to further aspects of the disclosure. Device 70 may be similar in function to device 10. In such a manner, device 70 may include band 12 (FIGS. 8, 12A, and 12B), electrodes 14, leads 16, and a stimulator 18. However, as shown, device 70 may include substrate 60. FIG. 8 is a view of device 70 positioned on a subject, while FIG. 9 illustrates device 70 with band 12 removed so as to illustrate additional components of device 70. FIG. 10 illustrates device 70 without band 12 or stimulator 18, while FIG. 11 illustrates substrate 60 including various printed components on substrate 60. FIGS. 12A and 12B are exploded perspective views of device 70. As noted above, substrate 60 may be made of mylar, polyester, or other suitable material. Substrate 60 may be suitability thin and flexible so as to conform to a portion of the subject's head (e.g., the forehead) and may optionally be adhesive. Electrodes 14 and leads 16 may be printed on the substrate 60, as noted above. In some examples, substrate 60 may include portions moveable with respect to other portions of substrate 60. That is, while substrate 60 is depicted as a monolithically formed one-piece construction, in other arrangements, the substrate may include a plurality of portions (e.g., two or more) coupled together (e.g., moveably coupled to one another, slidably coupled with respect to one another, etc.) through any appropriate means. In such an example, one or more of electrodes 14 and/or leads 16 may be printed on one portion of substrate 60 while one or more of electrodes 14 and/or leads 16 are printed on another portion of substrate. As such, spacing of electrodes 14 may be adjusted to accommodate a wide range of subject head sizes.

Further, as shown in FIG. 12B, substrate 60 may include a pad member 66. Pad member 66 may comprise one or more of a cushion or an adhesive member. Optionally, pad member 66 may be stretchable so as to accommodate preferred electrode 14 placement and different size subject heads. In addition, as shown in FIG. 9-12B, substrate 60 may include one or more coupling mechanisms 62 (e.g., posts 62) configured for coupling stimulator 18, including conductive portion 68, to substrate 60. Optionally, band 12 may include one or more coupling mechanisms 62 (e.g., posts 62) configured for coupling stimulator 18 to band 12. While posts 62 are depicted, the disclosure is not so limited. Instead, posts 62 may be supplemental to, or replaced by, any appropriate fastener such as, e.g., screws, snaps, nails, magnets, Velcro, and adhesives, etc. Posts 62 may cooperate (e.g., mate or correspond) with an appropriate coupling feature(s) 64 of stimulator 18. For example, coupling features 64 of stimulator 18 may include tapered channels. In use, stimulator 18 may be mounted to substrate 60 by positioning posts 62 in a first end (e.g., wider end) of coupling features 64 and moving stimulator 18 relative to substrate (e.g., downward) such that posts 62 move toward a second end (e.g., narrow end) of coupling features 64. In such a manner, posts 62 may be received within coupling features 64 via an interference fit so as to secure stimulator 18 to substrate 60 and band 12. Accordingly, while two posts 62 and two coupling features 64 are shown, device 70 may include any appropriate number of coupling mechanisms 62 and coupling features 64 without departing from the scope of this disclosure. In yet a further arrangement, stimulator 18 may be fixedly (e.g., permanently) coupled to band 12. In the arrangement of FIGS. 8-12B, stimulator 18 may be coupled directly to substrate 60, within band 12, such that device 70 may be free from extraneous wires, components, and/or materials to increase ease and comfort of use by a subject. Additionally, upon coupling stimulator 18 to substrate 60, conductive portion 68 may be positioned in direct contact with the ends 71 of printed leads 16 and/or electrodes 14 for communication therebetween. As shown in FIG. 11, four leads 16, each terminating in an end 71 at a center of substrate 60, may be printed on substrate 60. Each lead 16 may be associated (e.g., in communication with) one of electrodes 14. Upon attachment of stimulator 18, ends 71 may contact conductive portion 68 of stimulator 18. Additionally, in some arrangements, band 12 may be reusable, while substrate 60 and electrodes 14 are disposable.

In use, a subject may remove electrodes 14 (and/or substrate 60) from packaging materials, peel away any liners or the like to expose adhesive portions, if any, of electrodes 14 and/or substrate 60, and attach (e.g., stick, couple, etc.) electrodes 14 and/or substrate 60 onto the forehead in a desired location. Gentle pressure may be applied, if necessary, to ensure electrodes 14 and/or substrate 60 are successfully adhered to the skin of the subject. Additionally, stimulator 18 may be coupled (e.g., via coupling mechanisms 62, coupling features 64, or a combination thereof) to substrate 60 such that conductive portion 68 may communicate with leads 16 and/or electrodes 14. Additionally, the subject may maintain the position of one or more of electrodes 14 and/or substrate 60 with one hand, while stretching band 12 around substrate 60 and/or electrodes 14 with the other hand to hold substrate 60 and/or electrodes 14 firmly in place for use.

Waking State

The stage of an individual's sleep cycle at the time of waking up is critical. In this regard, if an individual is awakened during, for example, deep sleep, the individual will typically feel groggy and disoriented upon wakening. This phenomenon is referred to as sleep inertia. Sleep inertia typically lasts for a few minutes or up to half of an hour. However, sleep inertia can last longer, even for hours, particularly when a subject is chronically sleep-deprived (e.g., receiving less than the AASM recommend amount of sleep). Sleep inertia can impair an individual's ability to perform even simple tasks and can be a hazard to others when the impaired individual is driving or operating heavy machinery. However, if an individual is awakened near or at the end of a sleep cycle, such as near or at the end of REM sleep or during light sleep, one is much less likely to suffer from sleep inertia and more likely to wake up feeling refreshed.

Conventional waking mechanisms, such as alarm clocks, signal a subject to wake up without regard to the stage of the subject's sleep. It is not unusual for an alarm to sound when a person is in the middle of a sleep cycle or in deep sleep. When a subject is awakened at such points in the sleep cycle, the subject will typically suffer from sleep inertia.

The present disclosure provides systems, devices, and related methods that employ EEG, electrooculogram ("EOG"), and/or electromyogram ("EMG") technology to detect stages of sleep, and awaken a subject within a predetermined timeframe during an optimal stage of sleep such that the subject wakes up feeling better refreshed. Embodiments of the present disclosure generally comprise a system in which EEG technology is utilized to detect brain activity, EOG technology is utilized to detect eye movement, and/or EMG technology is utilized to detect muscle activity while a subject is asleep and, thereby, enable a determination to be made as to what stage of sleep the subject is undergoing at any given time. Embodiments of the present disclosure may further comprise an alarm system in which a subject is gently awakened during a predetermined timeframe that is of the subject's choosing, but that occurs at an optimal point in the subject's sleep cycle so that the subject wakes up feeling refreshed, rather than groggy, thereby avoiding sleep inertia.

One or more embodiments may comprise a monitoring device or devices (e.g., 10, 70) equipped with an EEG 73 (including, e.g., sensor 13 described above and shown in FIG. 2), EOG 75, and/or EMG 77 monitoring system. Devices 10, 70 of the present disclosure may further comprise an alarm system that awakens the subject. The alarm system may utilize gentle vibration, gentle electrical stimulation, and/or sound in order to awaken the subject.

In one embodiment, the monitoring device may comprise a headband equipped with an EEG monitoring system 73. The headband may be worn by a subject during sleep and may monitor the subject's brain activity, as described above in connection with device 10, 70. In this way, it may be determined what stage of sleep the subject is undergoing.

Device 10, 70, including EEG monitoring system 73, may be configured to determine when the subject has entered various stages of sleep, such as, for example, REM sleep. Device 10, 70 may be configured to determine when the subject is near or at the end of a sleep cycle, such as near or at the end of the subject's REM sleep or during the subject's light sleep.

Additionally or alternatively, the monitoring device may comprise a headband equipped with an EOG monitoring system 75. In this embodiment, device 10, 70 may be worn by a subject during sleep and may monitor the subject's eye movement via EOR monitoring system 75. In this way, it may be determined what stage of sleep the subject is undergoing. EOG monitoring system may be configured to determine when the subject has entered various stages of sleep, such as REM sleep. EOG monitoring system 75 may be configured to determine when the subject is at or near the end of a sleep cycle, such as, for example, at or near the end of the subject's REM sleep or during the subject's light sleep.

Additionally or alternatively, the monitoring device may comprise a headband equipped with an EMG monitoring system 77. In this embodiment, EMG monitoring system 77 may be worn by a subject during sleep and may monitor the subject's muscle activity. In this way, it may be determined what stage of sleep the subject is undergoing. EMG monitoring system 77 may be configured to determine when the subject has entered various stages of sleep, such as REM sleep. EMG monitoring system 77 may be configured to determine when the subject is at or near the end of a sleep cycle, such as, for example, at or near the end of the subject's REM sleep or during the subject's light sleep.

In one embodiment, the device 10, 70 may comprise more than one monitoring system. For example, the device 10, 70 may comprise a headband equipped with dual monitoring systems. Such dual monitoring systems may comprise, for example, EEG 73 and EOG 75 monitoring systems, EEG 73 and EMG 77 monitoring systems, or EOG 75 and EMG 77 monitoring systems. Further, device 10, 70 may comprise a headband equipped with at least three monitoring systems, wherein such monitoring systems include EEG 73, EOG 75, and EMG 77 monitoring systems.

With respect to the monitoring device, it may be portable and wireless. Additionally, it may be capable of being recharged by the subject when not in use (e.g., when the subject is not sleeping). Alternatively, or additionally, the monitoring device may be powered by a subject's smartphone, tablet, or other personal computing device. In one or more embodiments, the monitoring device may be synced with a smartphone, tablet, smart watch, computer, or other electronic device or system 80 (hereinafter referred to as "synced system 80"). Synced system 80 may have application software 85 capable of receiving and transmitting data wirelessly to the monitoring device. In other embodiments, the monitoring device may be connected to one or more additional devices via an internet or network connection. In some arrangements, the monitoring device may wirelessly communicate with a cloud-based device and data delivered from the monitoring device to the cloud may be analyzed at the cloud. In some embodiments, delivery and transmission of data may be done via a wired connection.

In some embodiments, the device 10, 70 may further comprise a light sensor 72. Light sensor 72 may be able to detect whether the lights are on or off in a room where the device 10, 70 is located. In one embodiment, light sensor 72 may be configured to determine if and/or when the lights have turned off in the room where the device 10, 70 is located. In these embodiments, a light turning off may be a trigger for one or more of EEG 73, EOG 75, and/or EMG 77 monitoring systems to begin monitoring. In some embodiments, the light turning off may be a trigger for the device 10, 70, synced system 80, and/or application software 85 to being recording EEG-related data. Alternatively, or in addition, a home automation system in communication with the synced system 80 or application software 85 may inform the device 10, 70 when the lights have been turned off, thereby similarly functioning as a trigger to begin monitoring brain activity. Device 10, 70, synced system 80, and/or application software 85 may detect when a subject's visual cortex has been shut off (e.g., if the eyelids have been closed). Optionally, device 10, 70 may include one or more electrodes for monitoring muscle contractions of muscles near or around the eye orbit to determine whether a subject's visual cortex has been shut off. Additionally or alternatively, device 10, 70 may determine that the subject's visual cortex has been shut off via one or more of EEG 73, EOG 75, and/or EMG 77 monitoring systems. When the device 10, 70 has detected that a subject's visual cortex has been shut off (e.g., via muscle contraction, based on EEG data received via EEG monitoring system 73, or the like), it may signal the synced system 80 or application software 85 to begin recording the subject's EEG-related data.

In one or more embodiments, once the device 10,70, synced system 80, and/or application software 85 has made a determination that the visual cortex has been shut off, a "Do Not Disturb" message may be received by the device 10, 70, synced system 80, and/or application software 85. Once the "Do Not Disturb" message is received, the device 10, 70, synced system 80, and/or application software 85 may block future incoming data, messages, notifications, or a combination thereof from being received or displayed on the synced system 80 and/or application software 85. In additional embodiments, the receipt of a "Do Not Disturb" message may also trigger the device 10, 70, synced system 80, and/or application software 85 to stop playback of audio, video, or other media. For example, if device 10, 70, synced system 80, and/or application software 85 determine that a subject has fallen asleep, device 10, 70, synced system 80, and/or application software 85 may toggle the subject's communication device (e.g., phone) to a "Do Not Disturb" mode to prevent incoming phone calls and/or text messages from audible alerts, vibrations, etc. Once the subject's visual cortex is determined to be active again, an associated signal may be received by the device 10, 70, synced system 80, and/or application software 85 to allow for incoming data, messages, notifications, or a combination thereof to be received or displayed on the synced system 80 and/or application software 85. That is, once device 10, 70, synced system 80, and/or application software 85 determine that a subject is awake, device 10, 70, synced system 80, and/or application software 85 may turn off the "Do Not Disturb" mode of the subject's communication device (e.g., phone) to permit incoming phone calls and/or text messages via audible alerts, vibrations, etc.

FIG. 14A shows one exemplary arrangement. As shown, device 10, 70 may be affixed to a subject. Further, device 10, 70 may be coupled (e.g., via a wired or wireless connection) to synced system 80. Such wireless connections may include connection through a wireless network, Bluetooth technology, Zigbee protocols, or other similar technology known in the art. Synced system 80 may be in communication with a software application 85. As described above, the device 10, 70 may receive inputs from a subject's brain activity and communicate data from those inputs to synced system 80.

Synced system 80 may also communicate with the software application 85, which may interface with device 10, 70 via the synced system 80. In some arrangements, software application 85 may be loaded on synced system 80. In other arrangements, synced system 80 may communicate with software application 85, stored on an another device (e.g., computer, etc.) over a network (e.g., a wireless network.)

In some arrangements, device 10, 70 may provide a gentle vibration, a gentle electrical stimulation, a sound, or combinations thereof. In such embodiments, device 10, 70 may include an alarm device 98 for producing vibrations, electrical stimulation, pulses, sound, and the like. Alarm device 98 may include any conventional means known in the art or developed in the future. While alarm device 98 is illustrated as a separate component in communication with device 10, 70, it is understood that alarm device 98 may be positioned on or contained within device 10, 70.

In other arrangements, alarm device 98 may include a wristband configured to emit gentle vibration, gentle electrical stimulation, and/or sound. Alarm device 98 may be configured to communicate with device 10, 70 via either a wired or wireless connection. As such, alarm device 98 may include a vibration inducing device (e.g., piezoelectric component), an electrical stimulator (e.g., electrode). Additionally or alternatively, alarm device 98 may emit one or more of pulses or audible sound, and the like. In one embodiment, the gentle vibration, gentle electrical stimulation, and/or sound of the alarm device 98 may be produced by a subject's smartphone, tablet, smart watch, computer, or other electronic device or system that is synced with the device 10, 70, either through a wired or wireless connection, as discussed above. As such, the smartphone, tablet, smart watch, computer, or other electronic device or system may be outfitted with one or more devices for producing vibrations, electrical stimulations, pulses, sound, and the like. Such devices may include any conventional devices known in the art.

In use, as shown in FIG. 14B, a subject may provide various windows of time in which the subject wishes to awaken from sleep at step 82. In this regard, the subject may program the device 10, 70 or synced system 80 for various periods of time. For example, the subject may wish to wake up at 7:00 a.m., plus or minus twenty minutes. Thus, for example, a subject may provide a window of time of approximately forty minutes in length, such as from 6:40 a.m. to 7:20 a.m., during which the subject wishes to awaken. A subject may provide various other windows of time to be awakened from sleep (the "awake window"), such as twenty-minute windows, thirty-minute windows, etc., as desired.

Next, the subject may wear the device 10, 70 while sleeping. During sleep, the subject's brain activity, eye movement, muscle activity, or combination thereof may be monitored by the EEG 73, EOG 75, or EMG 77 monitoring systems of device 10, 70 at step 84. At step 86, if device 10, 70 or synced system 80 determines that the subject has not reached the subject's predetermined awake window, the method will return to step 84. Upon a determination at step 86 that the subject has reached the beginning of the subject's predetermined awake window, however, device 10, 70 and/or synced system 80 may search for certain activity or signal patterns at step 88. In this regard, EEG monitoring system 73 of device 10, 70 or synced system 80 would search for brain activity similar, or within an interval of similarity, to brain activity that occurs near or at the end of the subject's sleep cycle. Example target points in a subject's sleep cycle include, but are not limited to, at or near the end of the subject's REM sleep or during the subject's light sleep. EOG monitoring system 75 of device 10, 70 or synced system 80 may search for eye movement corresponding to such eye movement that occurs near or at the end of the subject's sleep cycle, such as near or at the end of the subject's REM sleep or during the subject's light sleep. EMG monitoring system 77 of device 10, 70 or synced system 80 may search for muscle activity corresponding to such muscle activity that occurs at or near the end of the subject's REM sleep or during the subject's light sleep. Upon detecting that the subject is near or at the end of a sleep cycle, such as at or near the end of the subject's REM sleep or during the subject's light sleep, the EEG 73, EOG 75, and/or EMG 77 monitoring system of device 10, 70 or synced system 80 may automatically communicate with the alarm 98 to trigger commencement of gentle vibration, gentle electrical stimulation, sound, or combination thereof in order to awaken the subject at step 90. In the current example, the subject would be awakened at an optimal time during the subject's sleep cycle, helping to avoid sleep inertia. In contrast, if at step 88 it is determined that the subject is not near or at the end of a sleep cycle, the method may return to step 86.

After a subject has been utilizing one or more devices of the present disclosure for a period of time, such as, for example, for a few nights of sleep, synced system 80 may be capable of recognizing a subject's repetitive sleep patterns and may allow the wakening device to automatically awaken the subject at a particular time each day based on such repetitive sleep patterns.

Personal Sleep Tracking

Further aspects of the present disclosure provide systems, devices, and related methods that employ EEG technology to detect stages of sleep in a subject and provide personal sleep tracking for a subject. As shown in FIG. 15, and described above, device 10, 70 may include a monitoring device or devices equipped with an EEG monitoring system 73. Such a monitoring device may be affixed to a subject during sleep via device 10, 70 and may monitor the subject's brain activity. In this way, a determination may be made as to what stage of sleep the subject is undergoing. As such, device 10, 70 may be configured to determine when the subject has entered various stages of sleep, such as, for example, NREM sleep, REM sleep, light sleep, or deep sleep. Further, device 10, 70 may be configured to determine when the subject is at or near the end of a sleep cycle, such as at or near the end of the subject's REM sleep or during the subject's light sleep. In some arrangements, device 10, 70 may be configured to determine when the subject begins to fall asleep or begins the process of waking up. Additionally, device 10, 70 may be configured to calculate a subject's total actual sleep.

As described above in connection with FIG. 14A, application software 85 in communication with synced system 80 that processes a subject's EEG data and utilizes such information for various purposes, such as providing personal sleep tracking information, customized outlooks, and guidelines for a subject to help facilitate better overall sleep and promote a healthy lifestyle. In one arrangement, application software 85 is in communication with synced system 80 for storing data collected by the EEG monitoring system 73. Such data may include, for example, the EEG data of the subject to be provided to the subject or otherwise mined for valuable data.

In use, a subject may put on device 10, 70 (including EEG monitory system 73) prior to going to sleep and would continue to wear device 10, 70 while sleeping. While wearing device 10, 70, EEG monitoring system 73 may monitor and collect the subject's brain activity. This data may then be stored by application software 85 and/or synced system 80. Subsequently, this data may be used for various purposes, including, but not limited to, providing highly accurate sleep tracking data for a subject, and providing customized outlooks and guidelines for the subject to facilitate higher quality sleep and promote a healthy lifestyle.

In one aspect, a "Personal Forecast" 91 may be provided to a subject via synced system 80. Such a forecast 91 may be based on the EEG-generated data from EEG monitoring system 73 and may help a subject to understand the amount and/or quality of sleep the subject receives on a given night. The forecast also may be based on other criteria in addition to EEG-generated data, such as, for example, data generated by wearable fitness or health trackers, dietary intake data, exercise data, or other data inputs entered either manually by a user or transmitter from another device or application. In one arrangement, personal forecast 91 may include a "pop-up" screen which may appear when the subject wakes up, the subject's alarm goes off, or when a combination of triggering events occurs. The pop-up screen may include a message indicative of the subject's sleep quality and quantity. In this and other embodiments, an outlook for the day based on the EEG-generated data may optionally be provided. In at least one embodiment, a graphical representation of a battery may be included to indicate how fully charged the subject is, e.g., the subject's "personal battery" 92. Much like a "weather forecast," personal forecast 91 and/or personal battery 92 may provide the subject an indication of how his or her day will go based on how well rested the subject is to start the day. This gives the subject the ability to modify behavior based on the amount or quality sleep received.

In one or more embodiments, a "Sleep Alarm" 93 feature may be provided. In some embodiments, a subject's actual sleep versus the subject's total time in bed is taken into account. Based on the subject's EEG data from EEG monitoring system 73, it can be determined how long it takes the subject to fall asleep from the time EEG monitoring system 73 is affixed to the subject until the monitoring device detects a signal that indicates the subject is sleeping. Similarly, based on the subject's EEG data, it also can be determined how many wake periods (and for how long) the subject had in the night. Accordingly, total actual sleep can be calculated based on such information. Calculating total actual sleep facilitates Sleep Alarm 93 which wakes the subject, when and only when the subject has actually slept for a predetermined amount of time (e.g., seven hours, even if the subject was in bed for eight hours). This feature may include a latest wake up time as well, regardless of the total actual sleep received by the subject, since some subjects will need to wake up at a given time (e.g., for work, school, or other appointment). Alternatively, the subject may have Sleep Alarm 93 wake the subject only if they have achieved a certain amount of REM sleep, deep sleep, or a combination of total, REM, and deep sleep.

In one or more embodiments, a "Smart to Bed" 94 feature may be provided where the EEG data indicates that the subject got less than the optimal, recommended, or predetermined amount of sleep the previous night. In some embodiments, the exact size of the deficit may be calculated and factored into a "Smart to Bed" 94 alarm the following night to prompt the user that it is "Time for bed." In these and other embodiments, the system may either dictate to the subject what amount of sleep (e.g., four hours of deep sleep, 2 hours of REM sleep, or some other amount based on the subject's age, gender, health profile, or recommendations from the AASM), or the subject may select its own preferred amount of sleep. Based on these predetermined criteria, for example, the amount or quality of sleep the subject is seeking may be determined. In other words, the EEG data may dictate a customized "Go to Bed" prompt that may factor in a subject's previous night's sleep data and optionally the subject's preferred wake up time (which can be derived from the time set for the morning alarm). Optionally, EEG monitoring system 73 may send real-time EEG data to synced system 80 or application software 85 in communication with synced system 80, and adjust the subject's wake up time dependent on the subject's total actual sleep patterns.

In one embodiment, a "Complete Health Picture" 95 may be provided. For example, a subject's workouts or other data, such as food intake, vitamin consumption, sun exposure, or other health monitoring information (e.g., heart rate, pulse, glucose levels) may be uploaded or shared with synced system 80 or application software 85 in communication with the synced system. The uploaded or shared data may be analyzed by synced system 80 or application software 85. Synced system 80 may then communicate to the subject, based on the subject's previous night's sleep, how well the subject will likely perform that day and optionally how well the subject will sleep in the next sleep session. Ultimately, all health inputs (e.g., exercise, diet, sleep) may be collected into a single repository of data collection in order to provide the subject with more insight into the subject's overall health and the impact of sleep quality and quantity.

In a further arrangement, a "Sleep Counseling" feature 96 may be provided. Accordingly, a subject's EEG data from EEG monitoring system 73 may be taken into account and counseling or screening advice may then be provided to the subject based thereon. For example, the device 10 may detect that subject wakes up at 2:00 a.m. for thirty or sixty minutes either one night in particular or repeatedly. In such a case, application software 85 may be configured to recognize this instance or pattern, and message the subject accordingly. In such a case, a pop-up screen may appear (e.g., via synced system 80) stating that the system has noticed that the subject has done this once or twice or has had a pattern of doing so. The pop-up may state, for example, "In our experience, this typically occurs if one has had one of three things after 5/6 p.m.: caffeine, nicotine, or alcohol." Thus, the pop-up may ask "Are you having one of those things after 5/6 p.m.? If so, eliminating those activities after 6:00 p.m. has been shown to significantly improve sleep quality." Another aspect of the sleep counseling feature 96 includes a comparison of EEG patterns of the subject with EEG patterns of "healthy sleepers" as well as those suffering from sleeping disorders, for example, insomnia or sleep apnea. By applying machine learning to analyze and detect patterns, differences, and similarities, it is possible to formulate correlations or indications of various sleeping disorders and communicate that information to the subject, a designated health care provider, a designated caretaker, or combinations thereof.

FIG. 15 illustrates one exemplary system. As shown in FIG. 15, device 10, 70 (including EEG monitoring system 73) may be affixed to a subject and coupled to synced system 80, such that information may pass between the device 10, 70 and synced system 80. In the arrangement shown in FIG. 15, synced system 80 is also coupled to the subject's refrigerator 97 and exercise equipment 99. In the shown embodiment, synced system 80 may be coupled wirelessly to the exercise equipment 99 and refrigerator 97, although embodiments where synced system 80 is coupled via a wired connection are also contemplated. Any suitable connection which allows for the transfer of information between the exercise equipment 99 or refrigerator 97 and synced system 80 may be used. Synced system 80 may communicate with exercise equipment 99 or refrigerator 97 to collect data on a subject's exercise or eating habits, respectively. This data may be used with the sleep data collected by device 10, 70 such that synced system 80 may provide a complete health picture 95.

Sleep Disorder Detection

In further arrangements, systems, devices, and related methods of the present disclosure may provide sleep tracking and sleep disorder detection for a subject. In such an arrangement, device 10, 70 may include EEG monitoring system 73. As described above, device 10, 70 may be affixed to a subject during sleep and may monitor the subject's brain activity. Based on the data, collected by the EEG monitoring system 73 regarding the subject's brain activity, a determination may be made as to what stage of sleep the subject is undergoing. For example, device 10, 70 may be configured to determine when the subject has entered various stages of sleep, such as NREM sleep, REM sleep, light sleep, or deep sleep, and/or when the subject is near or at the end of a sleep cycle, such as, by way of non-limiting example, at or near the end of the subject's REM sleep or during the subject's light sleep. In some arrangements, device 10, 70 may be configured to determine when the subject has begun to fall asleep or has begun the process of waking up. Device 10, 70 may also be configured to determine a subject's total actual sleep.

One or more aspects of the present disclosure may further comprise application software 85 in communication with synced system 80, as described above, and which may process the subject's EEG data and compare it to EEG data obtained from reference individuals or younger versions of the subject (referred to herein as "comparative EEG data"), in order to detect possible sleep disorders in the subject. The comparative EEG data may be obtained from individuals who have been predetermined not to have any sleeping disorder or from individuals who have been pre-diagnosed with one or more sleep disorders, such as sleep apnea or various other sleep disorders that may fall in the recognized sleep disorder categories of insomnias, hypersomnias, sleep-related breathing disorders, circadian rhythm sleep-wake disorders, parasomnias, or sleep-movement disorders.

In one or more embodiments, a subject (e.g., a subject with a potential sleep disorder) may affix device 10, 70 prior to going to sleep and would continue to wear to device 10, 70 while sleeping. In some embodiments, the subject may utilize device 10, 70 without the assistance of others, if desired. In use, device 10, 70 may monitor and collect the subject's brain activity (e.g., via EEG monitoring system 71). The data collected may then be stored by the synced system 80, or optionally, by the previously described application software 85. After EEG data has been obtained from the subject, the subject's EEG data may then be compared to pre-collected comparative EEG data using one or more defined algorithms. Upon comparing the sets of EEG data, a determination may be made by the application software 85 as to whether the subject has a possible sleep disorder, such as, for example, sleep apnea. Thus, for example, if device 10, 70 or synced system 80 determines, using the defined algorithms, that the subject's EEG data more closely resembles the comparative EEG data obtained from an individual with a sleep disorder than the comparative EEG obtained from a healthy individual, device 10, 70 or synced system 80 may determine that the subject has an indication of sleep apnea. In some embodiments, the determination as to whether the subject has a possible sleep disorder may include inputs in addition to EEG data, such as, for example, blood oxygen concentration, heart rate, EKG, or other data inputted manually by a user or transmitted from another device or application.

In some embodiments, after device 10, 70 or synced system 80 makes a determination as to whether the subject has a possible sleep disorder or a probability of a sleep disorder, such information may be communicated to the subject in various ways. For example, a probability as to whether the subject may have a sleep disorder may be provided to the subject via any applicable device, such as, a display of synced system 80. Such a probability may be one ranging from above zero percent to under one hundred percent. By way of example only, the monitoring device or synced system may compare subject data to comparative data and determine that the subject has a ninety-two percent probability of having a sleep disorder, such as, for example, sleep apnea. This probability may then be communicated to the subject. For example, a pop-up screen may appear via synced system 80 containing a simple message to indicate the subject's probability of having sleep apnea (e.g., "You have a 92% probability of having sleep apnea." or "You may want to visit your doctor, because you have an indication of sleep apnea.").

Figure 16:
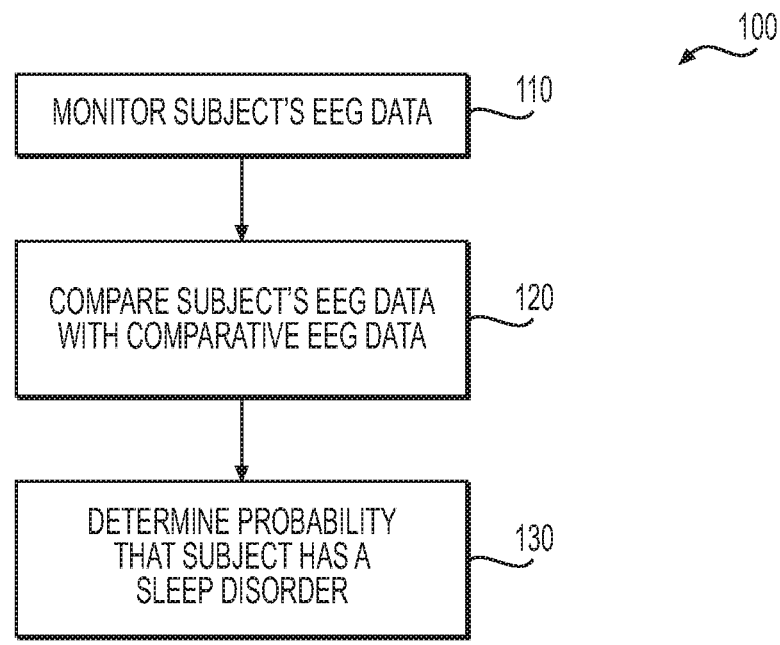
FIG. 16 illustrates an exemplary method of determining a probability that a subject has a sleep disorder.

FIG. 16 depicts a flow chart of an exemplary method 100 of determining a probability that a subject has a sleep disorder, according to the present disclosure. A system or device may monitor a subject's brain activity, collecting EEG data (step 110). EEG data may be collected, for example, via device 10, 70 (including EEG monitoring system 73). Next, the system or device may compare the subject's EEG data with comparative data obtained from reference individuals (step 120). Depending on the sleep disorder being analyzed reference individuals may include healthy individuals, individuals diagnosed with sleep disorders, and younger versions of the subject. Based on this comparison, the system or device may determine (e.g., via a comparison algorithm and/or machine learning) a probability that the subject has the sleep disorder and/or display such a probability to the subject via synced system 80 (step 130). Notably, device 10, 70 may be used to practice method 100 in the comfort of the subject's home or any other suitable environment of the subject's personal preference.

Thus, by applying machine learning to analyze differences and similarities and detect patterns, it may be possible to detect various sleep disorders in a subject and communicate that information to the subject. This can be beneficial for a variety of reasons. By way of example only, with such information, a subject with an indication of sleep apnea may be able to minimize the steps toward getting a corrective, therapeutic machine (e.g., CPAP machine). Similarly, for subjects in which systems of the present disclosure do not detect a possible sleep disorder, unnecessary doctors' visits may be avoided.

Dream Content Detection and Recall

In further arrangements, systems, devices, and related methods of the present disclosure may provide personal sleep tracking and possible dream content detection for a subject. In such an arrangement, device 10, 70 may include EEG monitoring system 73, as described above. Device 10, 70 may be affixed to a subject during sleep and may monitor the subject's brain activity. Based on the data, collected by the EEG monitoring system 73 regarding the subject's brain activity, a determination may be made as to what stage of sleep the subject is undergoing.

One or more aspects of the present disclosure may further comprise application software 85 in communication with synced system 80, as described above, and which may process the subject's EEG data and compare it to the subject's pre-recorded EEG data ("comparative subject data") and/or pre-recorded EEG data from other individuals ("comparative other EEG data")(collectively, "comparative EEG data") in order to detect possible dream content experienced by the subject and to trigger possible dream recall in the subject. The comparative other EEG data may be recorded at a sleep center/sleep lab, or the like, or may be recorded elsewhere. The comparative other EEG data may be stored electronically in various data repositories and may be capable of being accessed by and/or downloaded into application software 85 of synced system 80 by any suitable means.

The comparative EEG data may be obtained from the subject over the course of one or more nights of sleep and may be synced with dream content experienced by the subject, as entered in a dream log ("subject's dream data"). Alternatively or additionally, the comparative EEG data may be obtained from individuals other than the subject and may be synced with the subject's dream data, over the course of one or more nights of sleep.

While wearing device 10, 70, EEG monitoring system 73 may monitor and collect the subject's brain activity, and store the data via application software 85 in synced system 80. Upon waking up, the subject may record his or her dreams in a dream log or logs. The subject's dream data would then, in turn, be stored by application software 85 or synced system 80 using any suitable means known in the art. Following storage of the subject's EEG data and dream data, application software 85 may associate the subject's dream data of a given night with the subject's EEG data of the same night. In this way, particular dream content experienced by the subject may be linked to particular EEG patterns exhibited by the subject. For example, the subject may record in his or her dream log that he or she dreamt about swimming in the Pacific Ocean on a given night. For that same night, the subject's EEG data may include particular signals or patterns of signals (e.g., spikes) that may be tied to the subject's dream about swimming in the Pacific Ocean. As the amount of the subject's linked EEG data and dream data progressively increases over time as the subject continues to use device 10, 70 and log dreams, a larger amount of comparative subject EEG data may become available to be utilized.

In one embodiment, the comparative EEG data would be synced with dream content experienced by individuals other than the subject, as recorded in a dream log or logs ("reference dream data"), over the course of one or more nights of sleep. In one or more embodiments, in order to establish reference dream data, one or more individuals other than the subject may wear device 10, 70 prior to going to sleep and continue to wear the monitoring device while sleeping. While wearing device 10, 70, the EEG monitoring system 73 may monitor and collect the brain activity of such individuals. This data may then be stored by synced system 80 or application software 85. Upon waking up, the reference individuals may record their dreams in a dream log or logs. In one or more embodiments, the reference dream data would then be stored by synced system 80 or application software 85 using any suitable means known in the art. Following storage of the comparative EEG data and reference dream data, synced system 80 or application software 85 may associate such data so that the reference dream data of a given night would be tied to the comparative EEG data of the same night. In this way, particular dream content experienced by individuals other than the subject may be linked to particular EEG patterns exhibited by such individuals. Over time, the amount of comparative data available may progressively increase as individuals other than the subject continue to wear device 10, 70 and log their dreams.

After the desired EEG data has been obtained from the subject, the subject's EEG data would then be compared to other pre-collected comparative EEG data using one or more defined algorithms. Upon comparing the sets of EEG data, a determination may then be made by application software 85 as to whether the subject experienced particular dream content while sleeping. Thus, for example, if application software 85 determines, through algorithmic processing, that the subject's EEG data closely resembles comparative EEG data that corresponds to a person dreaming about water, application software 85 may determine that the subject experiences a dream pertaining to water.

Once synced system 80 or application software 85 makes a determination as to whether the subject may have experienced particular dream content, such information may then be communicated to the subject in various ways. In at least one embodiment, a pop-up screen may appear (e.g., via a display of synced system 80) containing a simple message (e.g., "Your dream involved water") to indicate possible dream content that the subject experienced while sleeping. This may be particularly useful for subjects who have difficulty remembering their dreams, and may help to prompt such subjects to recall further details about their dreams.

Thus, by applying machine learning to analyze differences and similarities and detect patterns, it is possible to detect various dream content and communicate that information to the subject. This can be beneficial for a variety of reasons, such as providing insight to the subject and/or amusement, excitement, and/or entertainment for the subject.

Without being limited by theory, it is believed that the ability to remember dreams may have to do with the timing of when a person wakes up. In this regard, if a subject is awakened while not dreaming or during deep sleep, dream recognition is less likely. Conversely, if a subject is awakened during a dream, in the middle of REM sleep, or near or at the end of a sleep cycle, such as at or near the end of REM sleep, or during light sleep, the subject is more likely to remember dreams.

Additionally, it is believed specific conditions occurring just prior to when an individual is woken up are correlated with dream recall (e.g., dream recognition), while other conditions may be associated with a lack of dream recall or an absence of dream experience. Activity in posterior cortical regions of the brain, including a bilateral parieto-occipital region encompassing the medial and lateral occipital lobe and extending superiorly to the precuneus and posterior cingulate gyms (a posterior cortical "hot zone") may be critical for dream recognition. In this regard, during both NREM sleep and REM sleep, local decreases in low-frequency (1-4 Hz) EEG activity in the posterior cortical hot zone are correlated with subjects reporting that they had experienced dreams, whether or not the subjects actually recalled their dreams.

Further, in NREM sleep, local increases in high-frequency (20-50 Hz) EEG activity in the posterior cortical hot zone, as well as in parts of the lateral frontal cortex and the temporal loves, are correlated with subjects reporting they had experienced dreams. Subjects who recall their dreams, compared to those who did not, also exhibit higher high-frequency EEG activity in medial and lateral frontoparietal areas. In REM sleep, increased high-frequency (25-50 Hz) EEG activity in the posterior cortical hot zone is correlated with dream recall and specific contents of dreams. Conversely, during both NREM and REM sleep, local increases in low-frequency (1-4 Hz) EEG activity in the posterior cortical hot zone are correlated with subjects reporting that they had not experienced dreams. See, e.g., Francessca Siclari, et al., entitled, "The Neural Correlates of Dreaming," NATURE NEUROSCIENCE, vol. 20, no. 6 (2017).

Many people set alarm clocks in order to be awakened at a desired time. However, alarms can negatively affect the likelihood of dream recall. For example, alarms will sound without regard to the stage of a subject's sleep, and it is not unusual for an alarm to sound and awaken the subject in the middle of a sleep cycle or in deep sleep. When this occurs, the subject may be less likely to be able to remember dreams. Although, this may be ideal for people who do not want to remember their dreams (e.g., chronic nightmare sufferers), for those who do want to remember their dreams this a problem. Conversely, if an alarm sounds and awakens a subject in the middle of REM sleep or at or near the end of a sleep cycle, such as at or near the end of REM sleep, or during light sleep, the subject is more likely to be able to remember dreams. Although this situation may be ideal for people who want to remember their dreams, the opposite is true for those who would rather forget their dreams (e.g., chronic nightmare sufferers).

In further arrangements, systems, devices, and related methods of the present disclosure may provide methods to awaken the subject at an optimal time such that the person is either more likely or less likely to remember his or her dreams, as desired. In such an arrangement, device 10, 70 may include EEG monitoring system 73, as described above. Device 10, 70 may be affixed to a subject during sleep and may monitor the subject's brain activity. Based on the data, collected by the EEG monitoring system 73 regarding the subject's brain activity, a determination may be made as to what stage of sleep the subject is undergoing. In addition, an alarm system 98 (as described above) may communicate with device 10, 70 via synced system 80 and/or application software 85.

Alarm system 98 may be configured to awaken a subject during a predetermined timeframe that is of the subject's choosing, but that occurs at an optimal point in the subject's sleep cycle so that the subject is either more likely or less likely to remember his or her dreams, based on the subject's personal preference. As described above, alarm device 98 may use gentle vibration, gentle electrical stimulation, sound, or a combination thereof in order to awaken the subject. In one embodiment, the gentle vibration, gentle electrical stimulation, or sound utilized by the alarm system may be delivered to the subject via device 10, 70 itself, or a wristband or the like.

In one embodiment, EEG monitoring system 73 of device 10, 70, synced system 80, and/or application software 85 may be configured to determine when the subject is exhibiting EEG activity characteristic of one or more neural conditions, sleep states, or sleep disorders. Additionally, EEG monitoring system 73 of device 10, 70, synced system 80, and/or application software 85 may be configured to determine when a subject begins to fall asleep, beings the process of waking up, and/or may be configured to determine the subject's total actual sleep.

As described above in connection with FIG. 14B, utilizing device 10, 70 may include a subject inputting various windows of time ("awake window") in which the subject wishes to awaken from sleep, if desired, at step 82 (so as to avoid alarm device 98 from prematurely awakening the subject at inopportune times (e.g., 3:00 a.m.)), even though desired conditions for wakening, as discussed herein, may be present.)

Next, the subject may wear the device 10, 70 while sleeping. During sleep, the subject's brain activity may be monitored by EEG monitoring system 73 of device 10, 70 at step 84. At step 86, if device 10, 70 or synced system 80 determines that the subject has not reached the subject's predetermined awake window, the method will return to step 84. Upon a determination at step 86 that the subject has reached the beginning of the subject's predetermined awake window, however, device 10, 70 and/or synced system 80 may search for certain activity, depending on how the subject prefers his or her dream recall ability to be affected.

In this regard, for subjects who desire to recall their dreams, the EEG monitoring system 73 may generally search for brain activity corresponding to such brain activity that occurs in the middle of, near, or at the end of the subject's sleep cycle, such as near or at the end of the subject's REM sleep or during the subject's light sleep at step 88. More specifically, with respect to activity during REM sleep, while the subject is in REM sleep, the EEG monitoring system 73 may search for brain activity associated with dream recall, including, but not limited to, a decrease in low-frequency EEG activity, an increase in high-frequency EEG activity in a posterior cortical hot zone including a bilateral parieto-occipital region encompassing the medial and lateral occipital lobe and extending superiorly to the precuneus and posterior cingulate gyrus, or an increase in high-frequency EEG activity in the frontal and temporal regions. With respect to activity during NREM sleep, while the subject is in NREM sleep, the EEG monitoring system may search for brain activity associated with dream recall, including, but not limited to, a decrease in low-frequency EEG activity, an increase in high-frequency EEG activity in the posterior cortical hot zone, an increase in high-frequency activity in the lateral frontal cortex and temporal lobes, or a higher high-frequency activity in the medial and lateral frontoparietal areas. Upon detecting that the subject is in the middle of, near, or at the end of a sleep cycle, such as near or at the end of REM sleep, or during the subject's light sleep, or detecting the more specific aforementioned activity occurring in REM sleep or NREM sleep, the EEG monitoring system 73 may automatically communicate with the alarm device 98 to trigger commencement of gentle vibration, gentle electrical stimulation, or sound in order to awaken the subject at step 90. In this way, the subject would be awakened at an optimal point in time during the subject's sleep cycle, such that the subject is more likely to remember dreams. In contrast, if at step 88 it is determined that the subject is exhibiting brain activity indicative that it is not ideal to awaken the subject, the method may return to step 86.

Similarly, for subjects who desire not to recall their dreams (e.g., chronic nightmare sufferers), upon reaching the beginning of the subject's predetermined awake window, EEG monitoring system 73 may generally search for brain activity corresponding to such brain activity that occurs while the subject is not dreaming, or during the subject's deep sleep or at another time associated with a lack of dream recall at step 88. More specifically, with respect to activity during REM sleep, while the subject is in REM sleep, the EEG monitoring system may search for brain activity associated with a lack of dream recall, including but not limited to, a decrease in low-frequency EEG activity in the posterior cortical hot zone that is unaccompanied by an increase in high-frequency EEG activity in the posterior cortical hot zone. With respect to activity during NREM sleep, while the subject is in NREM sleep, the EEG monitoring system may search for brain activity associated with a lack of dream recall, including but not limited to, a decrease in low-frequency EEG activity in the posterior cortical hot zone that is unaccompanied by an increase in high-frequency EEG activity in the medial and lateral frontoparietal areas. With respect to activity occurring during either NREM sleep or REM sleep, the EEG monitoring system may search for brain activity associated with an absence of dreaming, including but not limited to, increases in low-frequency EEG activity in the posterior cortical hot zone. Upon detecting that the subject is not dreaming or in deep sleep, or detecting the more specific aforementioned activity occurring in REM sleep or NREM sleep, EEG monitoring system 73 may automatically communicate with alarm device 98 to trigger commencement of gentle vibration, gentle electrical stimulation, or sound in order to awaken the subject at step 90. In this way, the subject would be awakened at an optimal point in time during the subject's sleep cycle, such that the subject is less likely to remember his or her dreams. In contrast, if at step 88 it is determined that the subject is exhibiting brain activity indicative that it is not ideal to awaken the subject, the method may return to step 86.

After a subject has been utilizing the devices, systems, and methods of the present disclosure for a period of time, such as for a few nights of sleep, for example, synced system 80 or application software 85 may be capable of recognizing a subject's repetitive sleep patterns and may allow devices 10, 70 of the present disclosure to automatically awaken the subject at a particular time based on such repetitive sleep patterns. As such, the devices, systems, and methods of the present disclosure may be particularly suitable for subjects with regular sleep patterns.

Sleep-Driven Automation

The temperature of approximately 98.6° F. (37° C.) is considered to be the average "normal" internal body temperature in human subjects. However, body temperature varies among individuals, and it is common for individuals to have "normal" internal body temperatures that deviate from 98.6° F. Indeed, it is widely understood that body temperatures in healthy adults may range from 97° F. to 99° F. Throughout the course of the day, it is normal for an individual's internal body temperature to fluctuate. Typically, internal body temperature rises during the earlier part of the day by one to two degrees, and then falls later in the day. However, internal body temperature may deviate from these norms, particularly depending upon the subject's activities or the environment. For example, body temperature typically rises in subjects performing strenuous exercise, while it falls in subjects who are exposed to cold environments.

Internal body temperature typically reaches its lowest point during REM sleep. During REM sleep, the temperature of a subject's sleep environment can particularly affect the subject's body temperature. This is because, during REM sleep, as compared to during other stages of sleep, the homeostatic process of thermoregulation may be less efficient.

An individual's internal body temperature can have a positive or negative impact on the quality of sleep. Human subjects typically experience better sleep when they reach their individual optimal internal body temperatures during sleep. A sleep environment that is either too warm or too cool may interfere with attaining optimal body temperatures and, in turn, interfere with the quality of sleep. Some individuals wake up frequently in the middle of the night with either sweats or chills. While this can be due to a variety of factors, such as stress, anxiety, or illness, it can also simply be caused by being in a sleep environment that is too warm or too cool for the individual's comfort. In this regard, a sleep environment's comfort controls may be set at a level that interferes with an individual's ability to attain optimal body temperature during sleep. For example, the thermostat may be set at a level that is either too low or too high for a given person, or a ceiling fan may be switched off when a given person would benefit from having the fan switched on. When this occurs, an individual may wake up either sweating or shivering. The individual may then go through several steps, such as getting out of bed, adjusting the comfort controls, returning to bed, and then attempting to go back to sleep. For some, this may cause such a substantial interruption in sleep that they have extreme difficulty returning to sleep, if at all. This may lead to sleep deprivation or other harmful sleep behaviors.

Generally, human subjects sleep better in cooler temperatures (typically 63° F.-67° F.). Some have used programmable thermostats to automatically lower the temperature in their homes at specific times. However, such programmable thermostats are not tailored to correspond to the specific temperature needs of individuals, which may vary from person to person, and may fluctuate during sleep.

Embodiments of the present disclosure include systems, devices, and related methods that utilize personal temperature and humidity/moisture monitoring devices to detect body temperature or perspiration levels of a subject and, based upon the gathered data, communicate with comfort control device(s) to automatically adjust the temperature or other comfort conditions of a sleeping environment to be better suited to the subject. In this way, embodiments of the present disclosure enable a subject to reach an optimal body temperature for sleeping, thereby facilitating better overall sleep for the subject.

Figure 17:
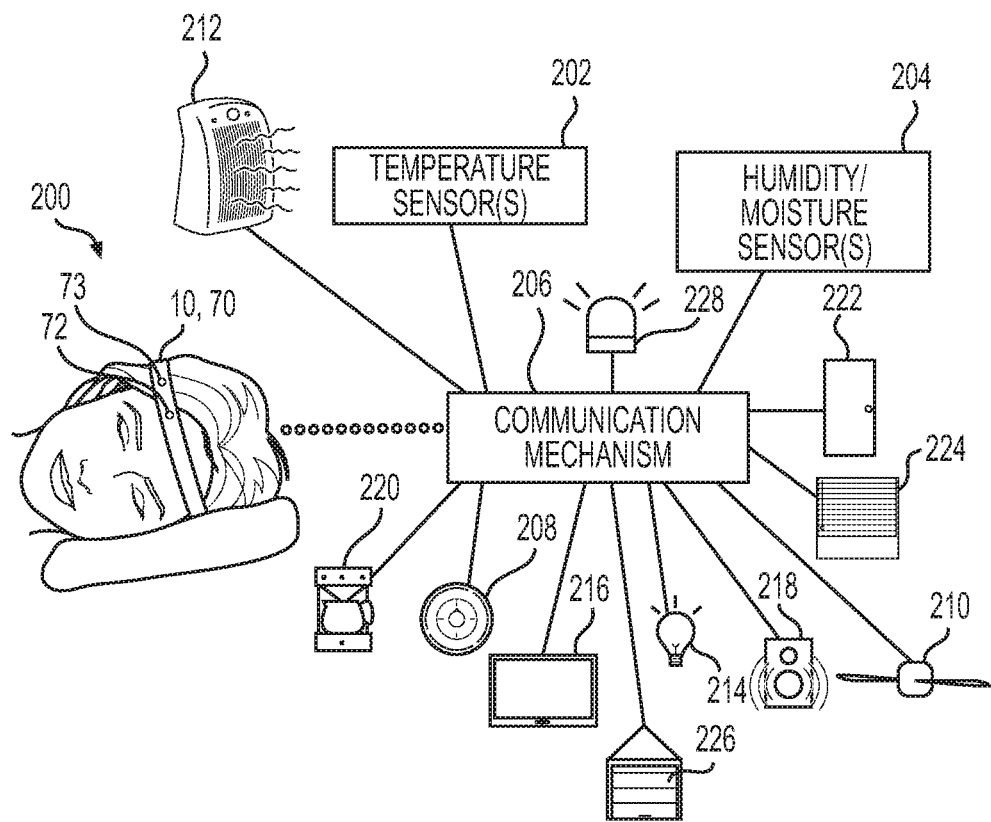
FIG. 17 illustrates an exemplary device in communication with a plurality of comfort control devices and/or household devices.

As shown in FIG. 17, an automated personal control system 200 may include a temperature sensor(s) 202 of a temperature monitoring device(s) and/or a humidity/moisture sensor(s) 204 of a humidity/moisture monitoring device(s). Temperature sensor 202 and humidity/moisture sensor 204 may be used to detect temperature and/or perspiration levels, respectively, while a subject is asleep to enable control system 200 to determine whether a subject is too hot or too cold for the subject's personal comfort, and accordingly, whether the comfort conditions of the subject's sleeping environment need to be adjusted.

Embodiments of the present disclosure may further include a communication mechanism 206 (e.g., a wireless connection). Communication mechanism 206 may communicate the subject's temperature data and/or perspiration level data to various comfort control devices 208, 210, 212 which, as a result, may self-adjust based on the data so that the temperature or other comfort conditions of the sleeping environment are altered to meet the comfort needs of the subject at a given time. Once a subject's body temperature and/or perspiration level has returned to optimal for sleeping, the comfort control devices 208, 210, 212 may automatically switch off or return to their previous settings. Connection mechanism may exist independently or via synced system 80.

In some arrangements, temperate sensor 202 and/or humidity/moisture sensor 204 may be in communication with, or located on device 10, 70. As such, device 10, 70 may be configured to determine the subject's optimal body temperature and/or perspiration level for sleeping by monitoring a subject's EEG-generated data and/or the temperature and/or humidity of the sleeping environment.

In one embodiment, the communication mechanism 206 may comprise a wireless connection between device 10, 70 and the subject's home automation system and/or specific comfort control devices 208, 210, 212. This allows device 10, 70 to be synced with such a home automation system and/or specific comfort control device 208, 210, 212. By way of example only, such comfort control devices may include the Nest Thermostat or other smart thermostat 208, a ceiling fan and/or a standing fan 210, a stand-alone heater and/or air conditioner 212, or other mattress, mattress topper, mattress pad, such as for example, a ChiliPAD™, electric blanket, or other bedding item capable of temperature control. Communication mechanism 206 may be adapted to transmit data between device 10, 70 and the subject's home automation system and/or specific comfort control device(s) 208, 210, 212. In one embodiment, the communication mechanism may comprise a wired connection between the monitoring device and the subject's home automation system and/or specific comfort control device or devices. One example arrangement is depicted in FIG. 17. As can be seen in FIG. 17, a monitoring device 10, 70 is affixed to a subject and is coupled to a comfort control device 80, such as an air conditioner. The monitoring device 10, 70 can monitor one or more of the subject's EEG, temperature, or perspiration level and communicate that information to the comfort control device 80. The comfort control device 80 may then, automatically or on instructions from a coupled device, adjust a condition (e.g., a temperature) of the subject's sleeping environment.

When using the devices, systems, and methods of the present disclosure, a subject may use device 10, 70 anywhere that the subject may fall asleep (e.g., bedroom, couch, recliner, futon, family room, living room, or basement). Accordingly, it may be useful for such individuals to put on device 10, 70 when they believe that they may fall asleep in the near future. This would apply to any activity during which a subject often falls asleep (and for which the subject would ideally want a corresponding adjustment of a comfort control device or devices).

Additional features of disclosure include the collection and storage of a subject's personal body temperature and/or perspiration level data obtained by device 10, 70. Such data may be associated with the subject's EEG data via EEG monitoring system 73, to be provided to the subject or otherwise mined for valuable data. For example, synced system 80 or application software 85 in communication with synced system 80 may be capable of establishing a correlation between the EEG data and body temperature so that observing a specific EEG pattern may result in a command being sent to one or more comfort control systems 208, 210, 212, to adjust environmental conditions even before a temperature change is detected by device 10, 70. Thus, for example, a subject's body temperature may fall at a certain point in time every night, accompanied by a specific EEG signal or signals. In such an instance, synced system 80 or application software 85 in communication with the synced system 80 may recognize the EEG signal pattern and may send a command to the home automation system or comfort control devices 208, 210, 212, to adjust conditions based on the subject's EEG data.

Still further, control system 200 may communicate with one or more household devices to automatically initiate certain home environment events as desired by the subject. As such, events within the subject's home environment occur at a given point in time or at a given point relative to the subject's sleep cycle. By way of example only, such automated household devices may include lighting 214, television sets 216, audio systems 218, coffee makers 220, door locks 222, window shades/blinds 224, garage doors 226, home alarms, and the like. Communication mechanism 206 may be adapted to transmit data between device 10, 70 and the subject's home automation system and/or various household device(s). In one embodiment, communication mechanism 206 may comprise a wired or wireless connection between device 10, 70 and the subject's home automation system and/or various household device(s).

When using embodiments of the present disclosure, a subject may provide various home environment events that the subject wishes to occur upon, or shortly after, falling asleep. Example home environment events may include, but are not limited to, switching off lights 214, switching off television sets 216, switching off audio systems 218, engaging door locks 222, closing garage doors 226, engaging home alarms 228, running higher energy load appliances (e.g., charging a car, washing machine, dryer, etc.) and the like. In addition, or alternatively, a subject may provide various home environment events that the subject wishes to occur upon waking up. Such home environment events may include, for example, switching on lights 214, switching on television sets 216, switching on audio systems 218, disengaging door locks 222, opening garage doors 226, disengaging home alarms 228, switching on coffee makers 220, raising window shades or blinds 224 and the like.

When using devices and systems of the present disclosure, a subject may put on device 10, 70 prior to going to sleep and continue to wear device 10, 70 while sleeping. At the time that the subject puts on device 10, 70, the subject may have various household devices in a particular state. For example, various household devices may be switched on, such as lighting 214, a television set 216, and/or an audio system 218. Alternatively, various devices may be disengaged, such as door locks 222 and home alarms 228. As another alternative, various devices may be open, such as window shades or blinds 224, garage doors 226, and/or pet transit doors. While wearing device 10, 70, EEG monitoring system 73 may monitor the subject's brain activity. Upon detecting that the subject has fallen asleep, device 10, 70 may communicate this data to the subject's home automation system or various household device(s) via communication mechanism 206 described herein to initiate the occurrence of various desired home environment events (e.g., switching off lights 214, etc.) Additionally or alternatively, the subject may desire that a various home environment event or events occurs upon the subject waking up. In this instance, upon detecting that the subject has begun the process of waking up, device 10, 70 may automatically communicate this data to the subject's home automation system or various household devices via communication mechanism 206, triggering the home automation system to switch on lights 214, etc.

In addition, systems and devices of the present disclosure may be configured with various parameters, as desired, to ensure that the home environment events do not occur at undesirable times. In this regard, with respect to waking up events, a subject may wake up in the middle of the night, perhaps needing to use the bathroom or for various other reasons. The monitoring device would detect that the subject was awake and may initiate such events as switching on lights 214 or starting a food or beverage maker (e.g., a coffee maker, hot water heater for tea, etc.) 220, which may be undesirable at that time. To avoid this, the device may be configured to only trigger desired waking up events in a predetermined window.

Similarly, devices and systems of the present disclosure may be configured with various parameters with respect to falling asleep events. For example, a subject may start falling asleep gradually and still be easily woken up. The monitoring device may detect that the subject was asleep and may initiate such events as switching off lights 214, a television set 216, an audio system 218, or similar devices, which may have the unintended effect of rousing a subject who has just started to fall asleep. To avoid unwanted occurrences of this, systems and devices may be configured to only trigger desired falling asleep events after a predetermined amount of time has elapsed since the subject began falling asleep. The predetermined amount of time may be a default amount of time, or an amount provided by the subject according to the subject's preference. Additionally or alternatively, the described devices and systems may be configured to only trigger falling asleep events after a specific desired time, such as 10:00 p.m.

In various embodiments, the devices and systems of the present disclosure may include additional features with respect to various home environment events. For example, where a television set 216 is triggered to switch off upon device 10, 70 detecting that the subject has fallen asleep, the home automation system may be configured to initiate a command to pause the program that the subject was watching prior to falling asleep. This may occur independently or via communication with a DVR, streaming service, or other video playback device. In this way, the subject may later pick up with the show after the sleep session. Further, in at least one embodiment, the home automation system may be configured to initiate a command to "rewind" the program that the subject was watching prior to falling asleep by a predetermined amount of time. Accordingly, the devices and systems of the present disclosure would be particularly suitable for subjects who slowly fall asleep, as this affects their memory of the period of time prior to falling asleep. The predetermined amount of time may be a default amount and/or an amount provided by the subject according to the subject's preference. For example, the amount of time may be thirty seconds, five minutes, or any other desired amount of time. The "rewind" command may be initiated after the subject's television set 216 has been switched off or after the volume has been silenced, so as not to arouse/awaken the recently asleep subject. In one embodiment, the volume may be lowered gradually over a predetermined period of time, such as a thirty seconds, five minutes, or any other desired amount of time, so as not to startle the subject by the abrupt ceasing of noise, prior to switching off the television set 216. Similarly, once the subject was detected to be falling asleep or recently asleep, the lighting 214 may be gradually dimmed, as opposed to abruptly turned off so as to avoid rousing the subject.

While the present disclosure has been particularly shown and described with reference to preferred embodiments thereof, it will be understood by those skilled in the art that the foregoing and other changes in form and details may be made therein without departing from the spirit and scope. For example, while some embodiments refer to home automation systems and home environment events, it should generally be understood that substantial benefit may be derived from embodiments of the present disclosure outside of the home. In this regard, for example, some individuals may sleep in their offices or other work environments from time to time, particularly if working long hours. Thus, for example, a building automation system may be employed instead of a home automation system, initiating the occurrence of various building environment events suited to that particular building environment.

We claim:

1. A method for communication with a device, comprising:
    monitoring brain activity of a subject via an EEG monitoring system coupled to the subject;
    detecting a change in brain activity of the subject;
    comparing a first time with a predefined window of time;
    determining that the first time is within the predefined window of time;
    wherein based on the detecting the change in brain activity and the determining that the first time is within the first predefined window of time, wirelessly transmitting instructions to the device from the EEG monitoring system to dynamically adjust a setting of an environment of the subject via the device; and
    storing the monitored brain activity and the change in brain activity of the subject via a system synced with the EEG monitoring system.

2. The method of claim 1, wherein the setting of the environment includes a temperature of the environment.

3. The method of claim 1, wherein the device includes at least one household device, and wherein dynamically adjusting the setting of the environment includes changing an on/off setting or a level setting of the at least one household device.

4. The method of claim 1, wherein detecting the change in brain activity includes detecting that the subject is falling asleep or that the subject is waking up from sleep.

5. The method of claim 3, wherein the at least one household device includes one or more of a thermostat, an HVAC system, a fan, a heater, a light, a television, a mobile phone, an audio system, a beverage maker, a door lock, a window covering, a garage door, or an alarm.

6. The method of claim 1, further comprising:
    comparing a second time with the predefined window of time;
    determining the second time is not within the predefined window of time;
    wherein based on the detecting the change in brain activity and the determining the second time is not within the predefined window of time, delaying wireless transmission of instructions to the device from the EEG monitoring system to dynamically adjust the setting of the environment of the subject via the device.

7. A method for communication with a device, comprising:
    monitoring at least one of a temperature or a perspiration level of a subject via a wearable element coupled to the subject;
    after the monitoring of the at least one of the temperature or the perspiration level of the subject, comparing a current time with a predefined window of time;
    based on the comparing, determining that the current time is within the predefined window of time;
    wherein the device includes a household device in communication with the wearable element; and
    based on the monitoring of the at least one of the temperature or the perspiration level of the subject and the determining that the current time is within the predefined window of time, the wearable element instructing the household device to change a mode of the household device, wherein the mode of the household device includes an on status, an off status, a sleep status, a pause status, or a level setting.

8. The method of claim 7, wherein the wearable element includes one or more of a piece of clothing or a bodily accessory.

9. The method of claim 7, wherein the at least one household device includes one or more of a thermostat, an HVAC system, a fan, or a heater.

10. The method of claim 7, further comprising:
after the monitoring of the at least one of the temperature or the perspiration level of the subject, comparing a second time with the predefined window of time;
based on the comparing, determining the second time is not within the predefined window of time; and
delaying the instructing the household device by the wearable element to change the mode of the household device.

11. A method for communication with a device, comprising:
monitoring at least one of a temperature or a perspiration level of a subject via a wearable element coupled to the subject;
after the monitoring of the at least one of the temperature or the perspiration level of the subject, comparing a current time with a predefined window of time;
based on the comparing, determining that the current time is within the predefined window of time;
wherein the device includes at least one household device, and based on the monitoring of the at least one of the temperature or the perspiration level of the subject and the determining the current time is within the predefined window of time, the wearable element instructing the at least one household device to adjust a setting of the at least one household device; and
storing the at least one of the temperature or perspiration level of the subject via a system synced with the wearable element,
wherein the wearable element includes a monitoring system configured to monitor the temperature or the perspiration level of the subject.

12. The method of claim 11, wherein the wearable element includes one or more of a piece of clothing or a bodily accessory.

13. The method of claim 11, wherein the at least one household device includes one or more of a thermostat, an HVAC system, a fan, or a heater.

14. The method of claim 11, wherein the setting of the at least one household device includes a level setting.

15. The method of claim 11, further comprising:
detecting whether the monitored at least one of the temperature or perspiration level is within a predefined range of temperatures or perspiration level,
wherein the wearable element instructing the at least one household device is further based on the detecting whether the monitored at least one of the temperature or perspiration level is within the predefined range of temperatures or perspiration level.

16. The method of claim 11, further comprising:
monitoring brain activity of the subject via the wearable element, wherein the wearable element includes an EEG monitoring system coupled to the subject;
storing the monitored brain activity of the subject via the system synced with the wearable element;
correlating EEG data received from the EEG monitoring system and the at least one of the temperature or perspiration level of the subject; and
based on the correlating, determining on or more patterns in the EEG data.

17. The method of claim 11, further comprising:
after the monitoring of the at least one of the temperature or the perspiration level of the subject, comparing a second time with the predefined window of time;
based on the comparing, determining the second time is not within the predefined window of time; and
delaying the instructing the household device by the wearable element to adjust the setting of the household device.

* * * * *